US010261000B2

(12) United States Patent
Showalter et al.

(10) Patent No.: US 10,261,000 B2
(45) Date of Patent: Apr. 16, 2019

(54) AUTOMATED SPECIMEN PROCESSING SYSTEMS AND MULTISTEP PROCESSING OF MICROSCOPE SLIDES

(71) Applicant: Ventana Medical Systems, Inc., Tucson, AZ (US)

(72) Inventors: Wayne A. Showalter, Tucson, AZ (US); Nathan Smith, Tucson, AZ (US); Paul Howley, Victoria (AU)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 262 days.

(21) Appl. No.: 15/272,331

(22) Filed: Sep. 21, 2016

(65) Prior Publication Data

US 2017/0010194 A1  Jan. 12, 2017

Related U.S. Application Data

(63) Continuation of application No. PCT/EP2015/056770, filed on Mar. 27, 2015.

(60) Provisional application No. 61/972,725, filed on Mar. 31, 2014.

(51) Int. Cl.
*G01N 1/31* (2006.01)
*B25J 9/16* (2006.01)
*G01N 35/00* (2006.01)
*G01N 35/10* (2006.01)

(52) U.S. Cl.
CPC ............ *G01N 1/312* (2013.01); *B25J 9/1666* (2013.01); *G01N 35/00029* (2013.01); *G01N 35/0092* (2013.01); *G01N 35/0099* (2013.01); *G01N 35/1002* (2013.01); *G01N 2001/317* (2013.01); *G01N 2035/00138* (2013.01)

(58) Field of Classification Search
None
See application file for complete search history.

(56) References Cited

U.S. PATENT DOCUMENTS

2007/0038491 A1\* 2/2007 Samuhel ................ G01N 1/312
  705/7.12
2013/0052331 A1\* 2/2013 Kram ................... G01N 1/2813
  427/2.11

(Continued)

FOREIGN PATENT DOCUMENTS

WO  2004074847 A1  9/2004
WO  2011060387 A1  5/2011
WO  2013071357 A2  5/2013

(Continued)

OTHER PUBLICATIONS

PCT International Search Report dated Jul. 21, 2015 for corresponding PCT Application No. PCT/EP2015/056770.

*Primary Examiner* — Kathryn Wright
(74) *Attorney, Agent, or Firm* — Eric Grant Lee

(57) ABSTRACT

Systems and methods that enable automated processing of specimens carried on microscope slides are described herein. Aspects of the technology are directed, for example, to automated specimen processing systems and methods for dispensing liquids onto slides. The system can concurrently or sequentially perform lock cycles. Each lock cycle can include lock steps for addressing respective slides to dispense liquid. The lock steps of different lock cycles can be synchronized to prevent any collision between dispensers.

15 Claims, 15 Drawing Sheets

(56) References Cited

U.S. PATENT DOCUMENTS

2014/0329270 A1* 11/2014 Favaloro ................ G01N 1/312
                                                        435/30
2015/0293341 A1* 10/2015 Kram ..................... G02B 21/26
                                                        359/395

FOREIGN PATENT DOCUMENTS

| WO | 2014102160 A1 | 7/2014 |
| WO | 2014102161 A2 | 7/2014 |
| WO | 2014102162 A1 | 7/2014 |
| WO | 2014102184 A2 | 7/2014 |
| WO | 2014105739 A1 | 7/2014 |
| WO | 2014105744 A2 | 7/2014 |
| WO | 2014105747 A2 | 7/2014 |

* cited by examiner

| Flow Number | Non-Staining (first) lock cycle time - secs | Number of specimens per lock cycle | Return time relative to $LC_1$ | Non-Staining (first) lock step time - secs | Staining (second) lock step time - secs | Staining (second) lock cycle time - min:secs | Maximum non-staining steps per staining step |
|---|---|---|---|---|---|---|---|
| abbrev: FN | FLC or $LC_1$ | n | FR | FLS or $LS_1$ | SLS or $LS_2$ | SLC or $LC_2$ | |
| formula: | | | | FLC/(n + FR) | (n + FR + FN) x (FLS/2) | SLS x (n + FR) x 2 | |
| +4 | 20 | 10 | 1 | 1.8 | 13.6 | 5:00 | 15 |
| -1 | 30 | 10 | 1 | 2.7 | 13.6 | 5:00 | 10 |
| +3 | 20 | 10 | 1 | 1.8 | 12.7 | 4:40 | 14 |
| -2 | 30 | 10 | 1 | 2.7 | 12.3 | 4:30 | 11 |
| +2 | 20 | 10 | 1 | 1.8 | 11.8 | 4:20 | 13 |
| +1 | 20 | 10 | 1 | 1.8 | 10.9 | 4:00 | 12 |

FIG. 12 ns and may additionally be designed with a disposable
AUTOMATED SPECIMEN PROCESSING SYSTEMS AND MULTISTEP PROCESSING OF MICROSCOPE SLIDES

CROSS-REFERENCE TO RELATED APPLICATIONS

This patent application is a continuation of International Patent Application No. PCT/EP2015/056770 filed Mar. 27, 2015, which claims priority to and the benefit of U.S. Provisional Application No. 61/972,725, filed Mar. 31, 2014. Each of the above patent application is incorporated herein by reference as if set forth in its entirety.

TECHNICAL FIELD

This disclosure relates to systems for preparing specimens for analysis. In particular, the disclosure relates to specimen processing systems and multistep methods for processing specimen-bearing microscope slides.

BACKGROUND

A wide variety of techniques have been developed to prepare and analyze biological specimens. Example techniques include microscopy, microarray analyses (e.g., protein and nucleic acid microarray analyses), and mass spectrometric methods. Specimens are typically prepared for analysis by applying one or more liquids (e.g., reagents) to the specimens. If a specimen is treated with multiple liquids, both the application and subsequent removal of each liquid can be important for producing stained specimens suitable for analysis. For example, microscope slides bearing biological specimens, e.g., tissue sections or cells, are often treated with a series of manually applied reagents to add color and contrast to otherwise transparent or invisible cells or cell components. This labor-intensive process often results in inconsistent processing due to individual techniques among laboratory technicians and often results in relatively low throughput.

"Dip and dunk" automated machines and automated pipetting systems are often used in laboratories to stain a large number of specimens. Dip and dunk automated machines can process specimens in batches by submerging racks carrying specimen-bearing microscope slides in open baths held in open containers. Unfortunately, carryover of processing liquids between containers leads to contamination and degradation of the processing liquids and inconsistent processing between batches. Worse, cells sloughing off the specimens can cause contamination of other slides in the liquid baths and can lead to misdiagnoses. Dip and dunk processes also utilize excessive volumes of liquids, resulting in relatively high processing costs when the reagents must be changed to reduce the possibility of specimen cross-contamination. The open containers are also prone to evaporative losses and reagent oxidative degradation that may significantly alter the concentration and effectiveness of the reagents, resulting in inconsistent staining characteristics between batches. Additionally, because all the slides in a single rack are dipped into the same baths, each slide is subjected to the same staining protocol, thus preventing individualized specimen processing. Accordingly, dip and dunk automated systems suffer numerous drawbacks. Automated pipetting systems have pipetting heads capable of individually dispensing liquids to specimens. To prevent contamination the pipette tip does not directly contact specimens and may additionally be designed with a disposable tip. To avoid collisions between pipetting heads, automated pipetting systems can be designed with a single pipetting head servicing a set of slides. Unfortunately, the speed of the single pipetting head design limits the systems throughput. Additionally, automated pipetting systems may be designed to dispense relatively small volumes precisely onto specimens in order to reduce the amount of fluid waste generated compared to dip and dunk systems.

Overview of Technology

At least some embodiments are directed to automated specimen processing systems configured to coordinate resources to processes specimen-bearing microscope slides. Algorithms can be used to determine schedules for various tasks to efficiently use the resources and consistently process specimens. In some embodiments, the automated specimen processing system includes movable dispenser apparatuses capable of performing lock cycles for dispensing liquid. The dispenser apparatuses may capable of colliding with one another. Accordingly, the lock cycles can be synchronized to avoid or limit collisions between the dispenser apparatuses and/or interference of the respective functions of the dispenser apparatuses. In one embodiment, an array of dispenser apparatuses can individually process a set of slides in series, parallel, or both, without physically contacting one another. Each dispenser apparatus can include two or more liquid dispensing mechanisms moved based on a dual-lock step protocol. For example, one dispensing mechanism can address slides based on one lock step protocol, and another dispensing mechanism can address the same slides based on another lock step protocol. The lock steps can be synchronized to coordinate movement of the dispensing mechanisms (e.g., dispensing mechanisms capable of colliding) to avoid collisions. The operation of the specimen processing system can also be controlled to avoid collisions between fluidic systems (e.g., staining dispenses, non-staining dispenses, etc.) and other systems, such as material handling components (e.g., slide transfer mechanisms, disposable transfer mechanisms, cover transfer mechanisms, or the like). The various tasks can be scheduled to provide desired throughput while avoiding interferences (including contacts).

The automated specimen processing systems, in some embodiments, include an array of dispenser apparatuses that include robotic pipettors and dispenser heads (e.g., dispenser heads capable of aspirating and dispensing streams of liquids for flooding slides). The pipettors can be positioned above the slides for dispensing, and the dispenser heads can be positioned laterally adjacent the slides for dispensing. In one embodiment, the dispenser heads can have one or two degrees of freedom, and the pipettors can have three degrees of freedom. For example, the dispenser heads can move linearly, and the pipettors can have three directions of linear motion. The robotic pipettors can include, without limitation, robotic arm assemblies configured to aspirate, hold, and dispense liquid.

An automated specimen processing system, in some embodiments, can determine lock steps using algorithms and can select tasks associated with the lock steps. Lock step processing can provide each slide with the same allocation of resources and can provide uniformity of timing or chemistry, or both, across slides for consistent staining, thereby enhancing reliability and repeatability of results. Lock steps can be staggered to prevent collision between moving components capable of physically contacting one another. In some embodiments, multi-lock step processing can include multiple lock steps for applying different liquids with different pipette heads. For example, dual-lock step processing can include two different lock step routines coordinated to provide simultaneous processing of multiple slides or sets of slides using afore described two or more independent liquid dispensing mechanisms. The lock steps can have uniform time durations to provide consistent processing between slides (e.g., slides in the same set, slides in different sets, etc.). The automated specimen processing system can determine collision-free travel paths, time-optimal travel paths, and/or coordinated motion of the robotic components.

At least some embodiments include dual-lock step processes with non-staining lock steps, staining lock steps, or other lock steps. At each non-staining lock step, a dispenser mechanism can be positioned to dispense non-staining liquid (e.g., one or more bulk fluids) onto one slide, or perform an alternative operation such as washing the dispenser. At each staining lock step, another dispenser mechanism can be positioned to dispense liquid (e.g., one or more fresh reagents or other liquids) onto one slide. The non-staining and staining lock steps can be coordinated to concurrently process multiple sets of slides. Additionally, the parameters (e.g., periods of time, order, etc.) of the non-staining lock steps can be different from the parameters (e.g., periods of time, order, etc.) of the staining lock steps. In some embodiments, non-staining lock steps can be repeated at a high frequency to frequently service each slide to, for example, replenish liquids to maintain minimum volumes of liquid on the slides. The staining lock steps can be repeated at a lower frequency because reagents may be applied less frequently. In some embodiments, a single staining lock step is performed for each set of non-staining lock steps. Thus, the dispenser mechanism for dispensing non-staining liquids addresses each slide more often than the staining dispenser mechanism.

In some embodiments, a method for processing specimen-bearing microscope slides held at slide processing stations comprises sequentially addressing the slides with a first dispenser by addressing each slide according to a first lock step. The first dispenser is movable relative to the slide processing stations and is configured deliver liquid onto the addressed slide. The slides are also sequentially addressed by a second dispenser. The second dispenser can addresses each slide according to a second lock step and is movable relative to the slide processing stations. In some embodiments, specimens are individually processed to perform different staining protocols on the specimens. The first lock steps can be scheduled with respect to the second lock steps to prevent any collision between the first and second dispensers while the first and second dispensers sequentially address the slides. After staining and under control from the lock step scheduler, the slides can be robotically transported away from the slide processing stations using, for example, a transport apparatus (e.g., a robotic arm, a transfer mechanism, etc.). The first and second dispensers can be positioned at dispense positions (e.g., next to the slides, above the slides, etc.) addressing and delivering liquid onto the respective slides. As these movements are allocated to a given lock step, they may also be scheduled in order to avoid possible collisions between different transport apparatuses. The operation of the staining stations can also be controlled to avoid interference, including collisions, between the dispensers and the stations when moving slides, handling opposable elements (e.g., covers/arcs for spreading fluid), manipulating liquids on slides, or the like.

An automated specimen processing system, in some embodiments, can include a scheduler module that selects operations and determines the order of the operations to control handling functions (e.g., rack transfer, barcode reading, slide drying, etc.) or other functions with, for example, specific timing requirements. The scheduler module can command components of the system to perform specimen processing, STAT processing of individuals slides or racks, or other types of processing. In some embodiments, the specimen processing system can alternate between different modes of operation depending on whether a user selects STAT processing, target throughput, or other target parameters. The scheduler module, in some embodiments, can include one or more algorithms, databases, and/or staining information. An algorithm can be selected based on, for example, desired staining characteristics, desired processing times, or the like. In some embodiments, one algorithm can be used to generate a schedule for dispensing non-staining liquids (e.g., wash solutions, solvents, deparaffinizing liquids, etc.) and another algorithm can be used to generate a staining schedule for dispensing reagents. Algorithms can also be used to synchronize tasks.

In one mode of operation, the scheduler module queues tasks and executes them in turn each time a resource is available within the context of a given lock step type (e.g., staining, non-staining, etc.). Such resources can include, without limitation, robotic arm assemblies, mixing stations, and other components. In some embodiments, the dual-lock step scheduler module can operate in a job-shop schedule mode of operation, in which tasks are distributed over a resource-time scale to process tasks in a predetermined amount of time. For example, the scheduler module can utilize all available resources at the same time to perform a task in the shortest amount of time. The job-shop schedule mode of operation can be used to devote all resources to a single slide processing station.

Schedules for controlling tasks in the context of specimen processing systems can include, without limitation, tasks for moving components, tasks for dispensing liquids, tasks for operating slide processing stations, tasks for moving items (e.g., racks, slides, opposables, etc.), and so forth. Schedules will run in the context of lock cycles for sequentially executing tasks in order to position dispenser apparatuses relative to slides. For example, a lock cycle can include lock steps for positioning dispenser mechanisms for dispensing liquid onto slides. Schedules for dispensing liquids can include dispense start and stop times. A schedule for operating slide processing stations can include, without limitation, tasks for rolling opposable elements along slides, an incubation task, a vacuum task (e.g., task for applying a vacuum to remove liquid), or the like.

In some embodiments, a method for processing specimen-bearing microscope slides includes delivering the slides to respective slide processing stations, repeatedly performing a first lock cycle that includes sequentially positioning a first dispenser at a plurality of first dispense positions for delivering liquid onto each of the slides, and performing a second lock cycle that includes sequentially positioning a second dispenser at a plurality of second dispense positions for delivering liquid onto each of the slides. Handling of slides can be scheduled to avoid any collisions between material handling components (e.g., slide handlers) when delivering the slides to the respective slide processing stations. The first and second lock cycles are scheduled to prevent any collisions between, for example, the dispensers (e.g., two staining dispensers, two non-staining dispensers, etc.) or other components (e.g., fluidic components, material handling components, slide transfer heads, etc.). In one embodiment, the first lock cycle includes delivering one or more streams of non-staining liquid from the first dispenser, and the second lock cycle includes delivering liquid from one or more robotic pipettors of the second dispenser. The highest frequency lock cycle (i.e., a 'non-staining' lock cycle) can be set based on physical limitations of the tasks associated with this lock step (e.g., time required to move bulk fluid robots or other non-staining hardware). The second frequency (i.e., a 'staining' lock cycle) can be set to a whole multiple (e.g., 1×, 2×, 3×, etc.) of the highest frequency, and can be selected to accommodate limitations of the tasks associated with this lock step (e.g., time required to aspirate and dispense reagents using staining hardware). In this manner the dual-lock step approach may be adjusted to accommodate various automated specimen processing systems.

In yet further embodiments, a method for processing specimen-bearing microscope slides comprises delivering a first set of specimen-bearing microscope slides to first slide processing stations. A second set of specimen-bearing microscope slides is delivered to second slide processing stations. A non-staining lock cycle is performed and includes moving a first non-staining dispenser sequentially to first dispense positions for dispensing liquid onto slides in the first set and moving a second non-staining dispenser sequentially to second dispense positions for dispensing liquid onto slides in the second set. A staining lock cycle is performed while performing the non-staining lock cycle and includes moving a first staining dispenser sequentially to first reagent dispense positions for dispensing reagent onto slides in the first set and moving a second staining dispenser sequentially to second reagent dispense positions for dispensing reagent onto slides in the second set. The non-staining lock cycle, in some embodiments, can include simultaneously delivering liquid onto pairs of the slides (e.g., one slide in the first set and one slide in the second set) until all the slides have received liquid. In other embodiments, three or more sets of slides can be simultaneously processed by two dispensers, three dispensers, four dispensers, and so forth. The staining lock cycle, in some embodiments, can include dispensing reagent liquid alternatively onto slides in the first set and slides in the second set. In some embodiments, alternatingly dispensing reagent includes (a) delivering reagent onto one of the slides in the first set; (b) after step (a), delivering reagent onto one of the slides in the second set; and (c) sequentially repeating steps (a) and (b) to deliver reagent onto most of or all the slides in the first set and most of or all of the slides in the second set. This process can be repeated to perform a wide range of staining protocols.

In some embodiments, an automated slide processing system includes a plurality of slide processing stations configured to hold respective specimen-bearing microscope slides, a non-staining dispenser apparatus, and a staining dispenser apparatus. The non-staining dispenser apparatus is movable relative to the slide processing stations and configured to sequentially dispense liquid onto the slides. The staining dispenser apparatus is movable relative to the slide processing stations and is configured to sequentially dispense reagent onto each of the slides. The automated slide processing system, in some embodiments, can include a controller in communication with the dispenser apparatuses. The controller can include a computer-readable medium containing instructions for performing a process comprising repeatedly performing lock cycles scheduled to prevent any collisions between the dispenser apparatuses.

At least some embodiments of the technology are directed to a system that contacts specimens with liquid by rolling opposable elements along slides. Distances separating non-planar (e.g., curved) wetted surfaces of the opposable elements and slides carrying the specimens is sufficient to form liquid meniscus layers (e.g., thin fluid films, bands of liquid, etc.) between the wetted surfaces and the slides. For example, a meniscus layer can contact at least a portion of a specimen and can be moved across the slide using manipulative action. Liquid can be dispensed onto the slides to maintain desired volumes of the meniscus layers movable via capillary action. Capillary action can include, without limitation, movement of meniscus layers due to the phenomenon of the liquid spontaneously creeping through a gap between the curved, wetted opposable surface and the slide due to adhesive forces, cohesive forces, and/or surface tension. The opposable element can manipulate (e.g., agitate, displace, etc.) the liquid to process the specimen using relatively small volumes of a liquid to help manage waste and provide consistent processing. Evaporative losses, if any, can be managed by dispensing to maintain a desired volume of liquid, reagent concentration, or the like.

BRIEF DESCRIPTION OF THE DRAWINGS

Non-limiting and non-exhaustive embodiments are described with reference to the following drawings. The same reference numerals refer to like parts or acts throughout the various views, unless otherwise specified.

FIG. 12 is a table of parameters for dual-lockstep processing in accordance with an embodiment of the disclosed technology.

DETAILED DESCRIPTION

Figure 1:
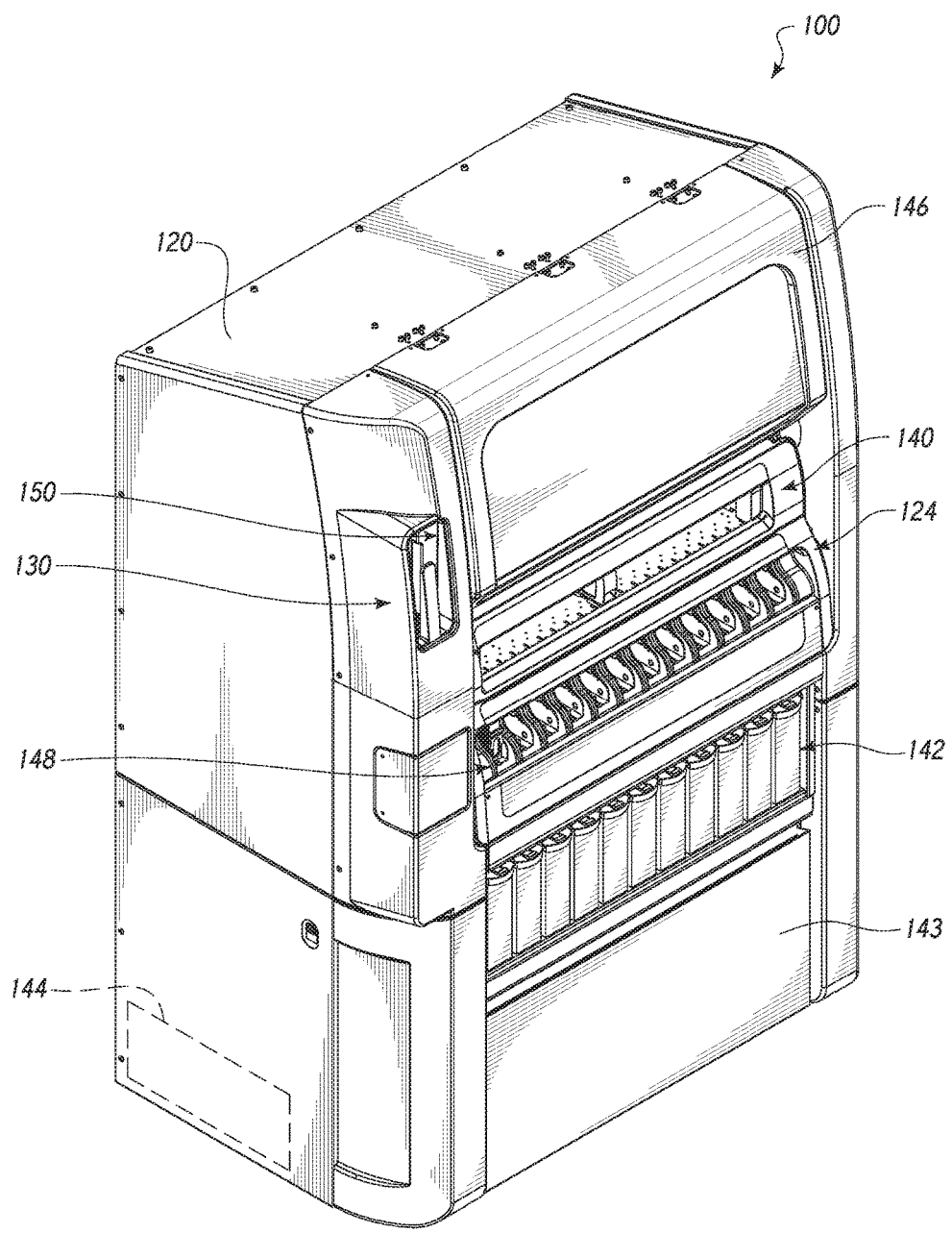
FIG. 1 is an isometric view of an automated specimen processing system in accordance with an embodiment of the disclosed technology.

FIG. 1 shows an automated specimen processing system 100 ("system 100") including a protective housing 120, a slide carrier parking station 124 ("parking station 124"), an opposable carrier loading station 130 ("loading station 130"), and reagent parking stations 140, 142. The system 100 can automatically process specimen-bearing slides using opposable elements ("opposables") loaded via the loading station 130 to perform, for example, specimen conditioning (e.g., cell conditioning, washing, deparaffinizing, etc.), antigen retrieval, staining (e.g., hematoxylin and eosin staining), or other types of protocols (e.g., immunohistochemistry protocols, in situ hybridization protocols, etc.) for preparing specimens for visual inspection, fluorescent visualization, microscopy, microanalyses, mass spectrometric methods, imaging (e.g., digital imaging), or other analytical or imaging methods. The slides can carry specimens throughout processing (e.g., baking through staining) for convenient handling while also preventing cross-contamination (e.g., contamination between slides). In one mode of operation, a batch of slides can be processed according to the same protocol. In another mode of operation, different slides of the same batch can be processed using different protocols. For example, the system 100 can individually process each slide with a unique staining protocol and optimize usage of its internal components to provide a relatively high throughput while maintaining processing consistency.

The protective housing 120 can inhibit, limit, or substantially prevent contaminants from entering an internal processing environment. The protective housing 120 can include a cover 146 that can be opened to access internal components, including, without limitation, fluidic components, slide processing stations, mixing components (e.g., mixing wells, reagent trays, etc.), slide carrier handling components, opposable carrier handling components, dryers, pressurization devices (e.g., pumps, vacuum devices, etc.), or the like.

The parking station 124 includes a row of bays. A slide carrier in the form of a basket is positioned in a left bay 148. Each bay can be configured to receive other types of slide carriers, such as racks, baskets, trays, or other types of carriers suitable for carrying slides before, during, and/or after specimen processing. The illustrated parking station 124 includes twelve bays separated by dividers. The number of bays, positions of bays, bay orientations, and bay configurations can be selected based on the types of slide carriers to be used and/or capacity of the system 100.

The loading station 130 includes a receiving opening 150 through which a user can load an opposable carrier. The opposable carrier can be a magazine that holds a stack of opposable elements. In other embodiments, the opposable carriers can be cartridges or other portable structures for carrying opposables.

Each parking station 140, 142 can include a row of bays, and each bay can hold one or more containers, including reagent containers, bottles, bag-in-box reagent containers, or the like. The bays of the parking station 140 can receive containers holding relatively small volumes, and the bays of the parking station 142 can receive containers holding relatively large volumes. For example, bulk liquid containers (e.g., containers holding wash solutions, solvents, etc.) can be loaded into respective bays of the parking station 142. Empty containers in the parking stations 140, 142 can be conveniently replaced with full containers.

A controller 144 can command system components and can generally include, without limitation, one or more processors, computers, central processing units, microprocessors, digital signal processors (DSPs), application-specific integrated circuits (ASICs), readers, and the like. To store information, the controller 144 can include, without limitation, one or more storage elements, such as memory (e.g., volatile memory, non-volatile memory, read-only memory (ROM), random access memory (RAM)). The stored information can include, without limitation, scheduler modules, algorithms, reagent recipes, lockstep information, heating programs, optimization programs, calibration programs, indexing programs, databases, and/or executable programs. Scheduler modules can be used to select operations for components and determine the order of such operations. The reagent recipes can be protocols for combining liquids to produce fresh reagents that will be dispensed onto slides. Lockstep information can include, without limitation, travel paths (e.g., collision-free travel paths of pipettors or other dispensers, time-optimal travel paths, etc.) and synchronization information, such as relationships between lock cycles, lock steps, etc. Optimization programs can be executed to optimize performance by, for example, reducing excess liquid consumption (e.g., reagent consumption), increasing productivity, decreasing waste, enhancing consistency of processing, or the like.

Figure 2:
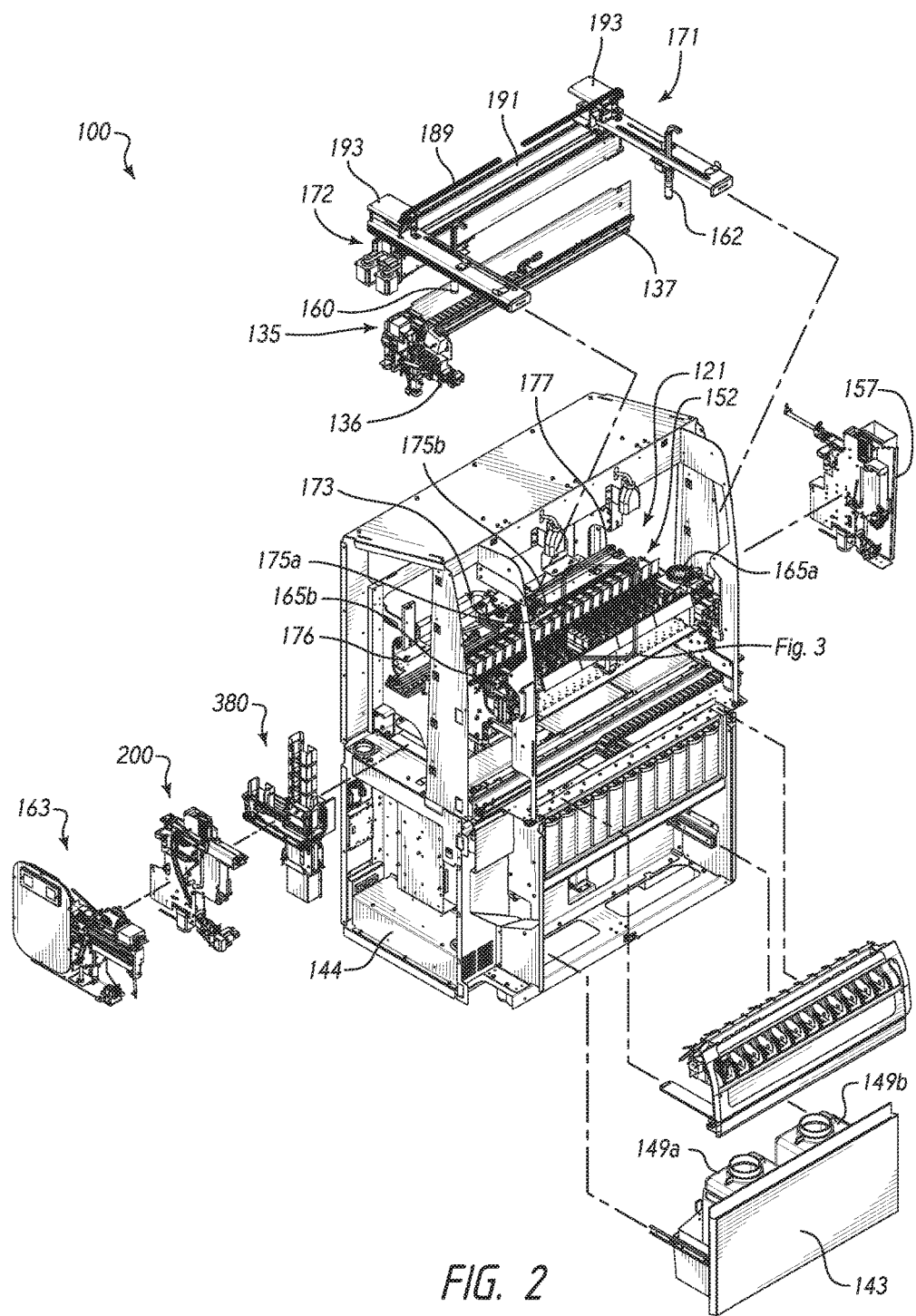
FIG. 2 is an exploded isometric view of the specimen processing system of FIG. 1. Portions of a protective housing are shown removed.

FIG. 2 is an isometric exploded view of the system 100 including a station 163, a slide ejector assembly 200, an opposable dispenser 380, and a specimen return mechanism 157. The station 163, slide ejector assembly 200, and opposable dispenser 380 are positioned at the left side of an internal environment 121. The specimen return mechanism 157 is positioned at the right side of the internal environment 121. A row 152 of slide processing stations can independently process biological specimens carried horizontally spaced-apart slides. The slide processing stations can be in a linear arrangement (illustrated in FIG. 2), a circular arrangement, or any other desired arrangement. A slide transfer apparatus 135 can include a transfer head 136 that carries slides to and from slide processing stations and a transport assembly 137 configured to move the transfer head 136. In some embodiments, the slide transfer apparatus 135 can be controlled according to a lock step (e.g., a staining lock step).

A liquid dispenser system 171 can include a dispenser apparatus 172 and a dispenser apparatus 173 (shown in the housing). The dispenser apparatus 172 can include dispensers in the form of robotic pipettors 160, 162 that can cooperate with one or more mixing stations 165a, 165b (collectively "mixing stations 165") to prepare and dispense liquids and, in some embodiments, is under control of the staining lock step. In some embodiments, including the illustrated embodiment, the pipettors 160, 162 can be independently moved to positions generally above the slides and can include, without limitation, one or more pipetting heads, pipettes (e.g., reusable pipette tips, disposable pipette tips, volumetric pipettes, micropipettes, etc.), aspiration tubes, or other fluidic components. The number and configurations of the robotic pipettors can be selected based on the number of slides to be simultaneously processed. In one embodiment, the dispenser apparatus 172 can have more than two pipettors (e.g., three pipettors, four pipettors, five pipettors, etc.) to process a large number of slides in parallel. To move the pipettors 160, 162, the dispenser apparatus 172 can include a transporter apparatus 189 that can include, without limitation, one or more rail assemblies (e.g., a rail 191 and carriages 193), robotic handlers, X-Y-Z transport systems, conveyors, drive motors, or other automated mechanisms or components. In other embodiments, the dispenser apparatus 172 can have a single pipettor.

The mixing station 165 can serve as a staging area to significantly increase processing capacity or otherwise enhance processing. The pipettors 160, 162 can obtain liquid at the mixing station 165 (e.g., liquid held in wells) and deliver the liquid onto the slides. Reactive reagents, such as reagents that react immediately upon mixing, can be mixed immediately before dispensing to enhance stain consistency and quality. Because reagents can be staged before they are needed, slide processing capabilities can be increased to provide high-volume automated slide processing.

Figure 3:
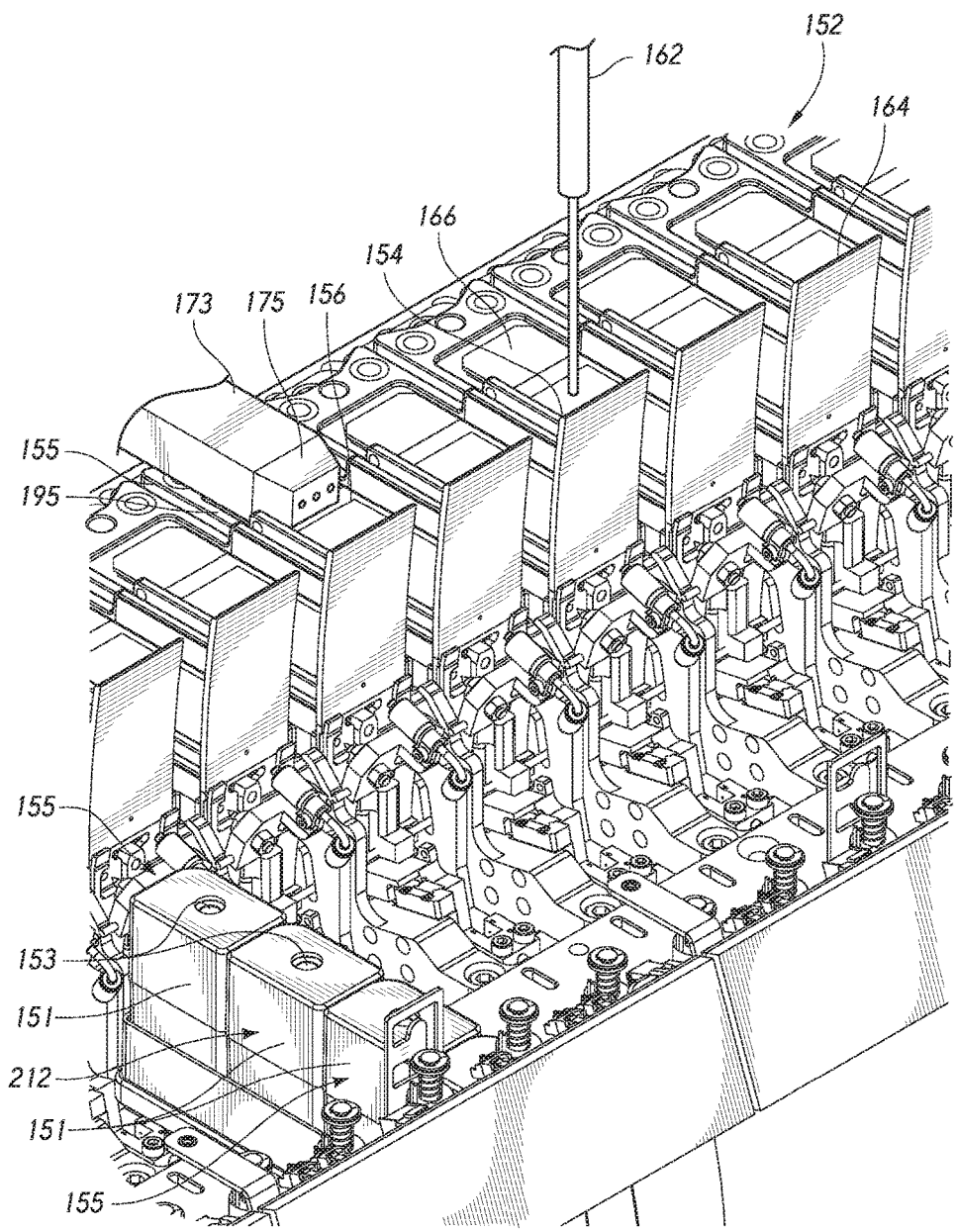
FIG. 3 is a detailed view of a portion of the specimen processing system of FIG. 2.

The dispenser apparatus 173 can include one or more dispensers in the form of dispenser heads 175a, 175b (FIG. 3 shows one dispenser head 175 positioned adjacent to a slide) and a transporter apparatus 176 configured to move the dispenser heads 175a, 175b. The dispenser head 175 can be configured to dispense liquid (e.g., non-staining liquid, supplemental liquid, etc.) onto one slide at a time and can include, without limitation, one or more orifices (e.g., jewel orifices), ports, nozzles, valves (e.g., one-way valves, check valves, pressure relief valves, etc.), sensors (e.g., pressure sensors, fluid detection sensors, etc.), pressurization devices (e.g., pumps), or other components for controlling liquid delivery. The transporter apparatus 176 can include, without limitation, one or more rail assemblies (e.g., a rail/belt assembly 177 in FIG. 2), robotic handlers, X-Y-Z transport systems, conveyors, drive motors, or other automated mechanisms for carrying items between locations. In some embodiments, the dispenser heads 175a, 175b can include a bank of dispenser heads configured to simultaneously or sequentially deliver streams of liquid directly onto slides, thereby washing or flooding the slide. The rail assembly 177 can move such bank of dispenser heads over or adjacent to a group of spaced apart slides. A fluidics module can deliver liquid from liquid sources, such as containers located at the parking stations 140, 142 of FIG. 1, to the dispenser apparatus 173.

FIG. 2 shows the waste drawer 143 holding waste containers 149a, 149b. A pneumatics module can deliver waste from slide processing stations to the containers 149a, 149b, which can be emptied periodically. Fluid movement into, out of, and within components can be controlled by a fluidics module that includes, for example, lines, pumps, valves, and/or filters. The pneumatics module can supply pressurized liquid (e.g., air) and generate vacuums to perform various slide processing operations and to move fluids throughout the system 100.

The system 100 can further include one or more transfer mechanisms that transport items between components and can include, without limitation, one or more robotic handlers (e.g., robotic arms), X-Y-Z transport systems (e.g., transport systems with rail assemblies and/or elevators), or other automated mechanisms capable of carrying items between locations (e.g., specimen-bearing slides to and from slide processing stations). In some embodiments, the transfer mechanism includes one or more end effectors, grippers, suction devices, holders, clamps, or other components suitable for holding items to carry the items to desired locations. For example, transfer mechanisms can transport slides and/or opposables to and from the slide processing stations.

FIG. 3 is a detailed view of a section of the row 152 of slide processing stations 155 (one identified in FIG. 3).

Specimen-bearing slides can lay on support surfaces of platens 195 (one identified in FIG. 3) of the slide processing stations 155, and an opposable element 154 (one identified in FIG. 3) can roll along the slide 156 to move liquid (e.g., thin films) along the slide 156 (one identified), mix liquids (e.g., mix two or more liquids on the slide), or otherwise manipulate liquids. Each slide processing station 155 can independently process a slide and can include, without limitation, one or more thermal elements (e.g., heaters, Peltier devices, etc.), actuators (e.g., opposable actuators), fluidics (e.g., fluid lines, valves, etc.), pressurization devices (e.g., pumps), fans, sealing members (e.g., sealing members for sealing against slides), sensors (e.g., slide detection sensors, pressure sensors, etc.), or the like.

FIG. 3 shows sealed containers 212 capable of holding relatively small volumes of reagent (e.g., about 10 mL to about 150 mL) and can have caps 151 with seal elements in the form of septums 153 that can minimize, limit, or substantially prevent evaporation losses. When the user installs the containers 212 in bays of the reagent parking station 140 (FIG. 1), septums 153 can be broken (e.g., pierced, torn, etc.) to establish fluid communication with the dispensers (e.g., pipettors 160, 162), which deliver the fluid to an appropriate slide and mixing stations (e.g., one of mixing stations 165a, 165b of FIG. 2), as well as deliver fluid from mixing stations to slides. This process can be under control of a staining lock step. The containers 212 can include, without limitation, one or more human readable labels, machine readable labels (e.g., a barcode to be read by the system), or other types of labels. The contents, holding capacity, and shape/configuration of the containers 212 can be selected based on the staining protocols to be performed.

In operation, a user can load slide carriers carrying specimen-bearing slides into the empty bays of the parking station 124 of FIG. 1 and can load opposable carriers carrying opposables into the loading station 130. The slide carriers can be transferred to a reader (e.g., a label reader, a barcode reader, etc.), not shown that reads labels, if any, on the slides. The slide carriers can be delivered to the station 163 of FIG. 2 which can include, without limitation, a dryer (e.g., a dehydration unit), a heating unit (e.g., a baking module), or other component capable of removing water from the slides, heating specimens (e.g., heating specimens to adhere the specimens to the slides), or the like. In some embodiments, the station 163 blows hot air over slides to dry the slides, and if the specimens contain paraffin, the hot air can soften the paraffin to promote adhesion of the specimens to the slides. An air system can partially recirculate air to control the humidity in the station 163. Slide carriers can be picked up and transported from the station 163 to another module (e.g., a slide processing station, a label reader, etc.) or returned to one of the bays of the parking station 124.

The slides can be delivered to the slide processing stations 155 and the dispenser head 175 delivers liquid onto the stationary microscope slides (e.g., slide 156 of FIG. 3). After the dispenser head 175 dispenses liquid onto one slide, the dispenser head 175 can be moved to sequentially address other slides. After the pipettor 162 dispenses reagent onto a slide, the pipettor 162 can be moved away from the slide to address other slides. A wide range of different liquids can be dispensed to perform different types of protocols. For example, the dispenser head 175 can dispense a non-staining liquid (i.e., a bulk fluid) and the pipettor 162 can dispense a staining liquid (i.e., a reagent). The movements of the dispenser head 175 and pipettor 162 are synchronized by the scheduler to prevent any collisions or interference. The movements can be based on timed sequences selected to achieve desired throughput, stain characteristics, etc. The timed sequences are part of lock cycles with lock steps for addressing the slides. One dispensing cycle can include lock steps for sequentially positioning the dispenser head 175 of FIG. 3 adjacent to the slide 156, and another dispensing cycle can include lock steps for sequentially positioning the pipettor 162 above the slide 156. The opposable element 154 can be used at various times to cover the slide 156 and minimize or limit evaporative losses, as discussed in connection with FIGS. 4-8.

The processed slides can be transported by slide transfer mechanism 135 from the slide processing stations 155 to the specimen return mechanism 157. The specimen return mechanism 157 can load specimen-bearing slides into a slide carrier, and the loaded slide carriers can be transported to the parking station 124. If the slide carriers are compatible with an automated coverslipper, a user can transport the slide carriers from the parking station 124 to an automated coverslipper for coverslipping. Alternatively, the slides can be manually coverslipped. The coverslipped slides can be analyzed using optical equipment, e.g., a microscope or other optical devices such as digital pathology readers.

The biological specimens disclosed herein can include one or more biological samples that can be a tissue sample or samples (e.g., any collection of cells) removed from a subject. The tissue sample can be a collection of interconnected cells that perform a similar function within an organism. A biological sample can also be any solid or fluid sample obtained from, excreted by, or secreted by any living organism, including, without limitation, single-celled organisms, such as bacteria, yeast, protozoans, and amebas, multicellular organisms (such as plants or animals, including samples from a healthy or apparently healthy human subject or a human patient affected by a condition or disease to be diagnosed or investigated, such as cancer). In some embodiments, a biological sample is mountable on a microscope slide and includes, without limitation, a section of tissue, an organ, a tumor section, a smear, a frozen section, a cytology prep, or cell lines. An incisional biopsy, a core biopsy, an excisional biopsy, a needle aspiration biopsy, a core needle biopsy, a stereotactic biopsy, an open biopsy, or a surgical biopsy can be used to obtain the sample.

Figure 4:
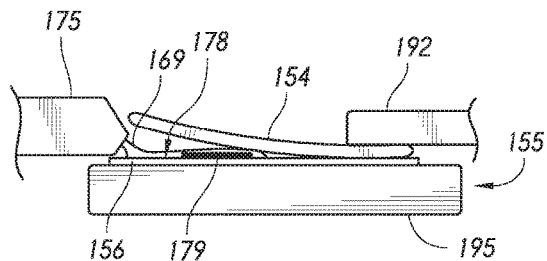
FIG. 4 is a view of liquid being dispensed onto a specimen-bearing microscope slide in accordance with an embodiment of the disclosed technology.
Figure 5:
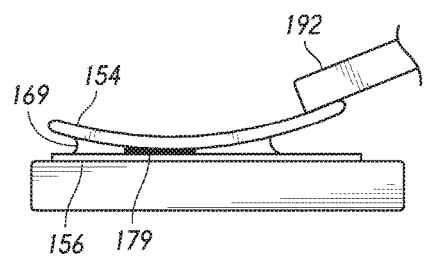
FIG. 5 is a view of liquid held between an opposable element and a slide.
Figure 6:
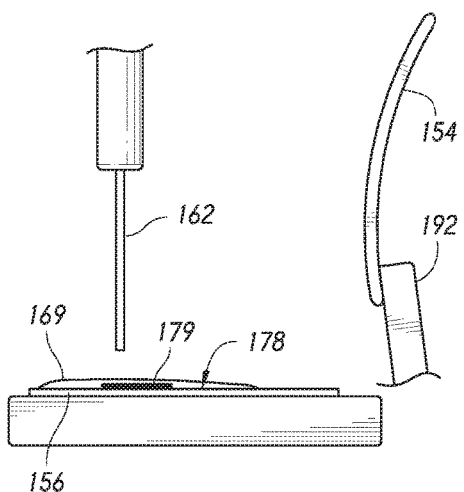
FIG. 6 is a view of a pipettor positioned above the slide.
Figure 7:
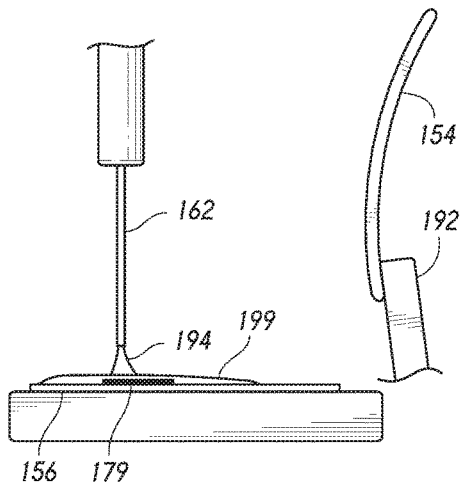
FIG. 7 is a view of the pipettor dispensing liquid onto the slide.

FIGS. 4-8 show stages of dispensing liquid and moving the liquid along the slide 156. FIG. 4 shows the dispenser head 175 during one lock step for addressing the slide 156, and FIGS. 6 and 7 show the pipettor 162 during another lock step for addressing the slide 156. The dispensing process of FIGS. 4-8 can be part of the processing discussed in connection with FIGS. 10-18.

FIG. 4 is a side view of the dispenser head 175 dispensing non-staining or bulk liquid 169 onto the slide 156 during a non-staining lock step in accordance with an embodiment of the disclosed technology. The stream of liquid 169 is delivered onto an upper surface 178 of the slide 156 which is held in a substantially horizontal orientation by the platen 195. The term "substantially horizontal" generally refers to an angle within about +/−5 degrees of horizontal, for example, within about +/−3 degrees of horizontal, such as within about +/−1 degrees of horizontal. The horizontal orientation of the slide 156 can help keep the liquid 169 on the slide 156. The slide 156 can be held at other orientations and positions.

FIG. 5 is a side view of the liquid 169 held between the opposable 154 and slide 156 as loaded onto a slide processing station (e.g. station 155 of FIG. 3). The slide processing station contains motor and heating units used to control the speed of motion of opposable 154 (e.g., about 10 mm/s to about 180 mm/s), and temperature of the slide 156 (e.g., about 37° C. to about 100° C.). In a dynamic mode of operation, an actuator 192 can roll the opposable 154 back and forth to repeatedly move a meniscus layer of the liquid 169 across the specimen 179. In some embodiments, the opposable 154 moves the liquid 169 while keeping an evaporation rate of the liquid 169 equal to or less than about a predetermined rate (e.g., 7 μL, per minute, 5 μL, per minute, or the like at about 37° C.). In a static mode of operation, the opposable 154 can remain generally stationary to perform, for example, incubation. The slide processing station can switch between dynamic and static modes to perform advance staining protocols. In some embodiments, the opposable rolling can be about 100 mm/s to provide a generally uniform temperature profile along the slide 156 at a given setpoint of the heater unit of the slide processing station. For example, at a target set point of 100° C., a roll speed of 180 mm/s can provide a temperature uniformity across the slide 156 within about 4° C. whereas a roll speed of 100 mm/s provides a temperature uniformity within about 6° C. The rolling direction, the rolling speed, and the rolling frequency can be adjusted depending on the characteristics of the applied liquid, desired temperature profile, and acceptable evaporation rates (e.g., a faster rolling speed may lead to higher evaporation rates).

FIG. 6 is a side view of the pipettor 162 positioned at a dispense position after the actuator 192 has moved the opposable 154 from a lowered position (FIG. 5) to a raised position (FIG. 6). The pipettor 162 can be positioned above a central region of the slide 156 to prevent dispensed liquid from falling off the slide 156. The volume of liquid 169 (e.g., a puddle or a film of the liquid) can cover most or all of the specimen 179, thereby limiting or preventing drying of the specimen 179. In other embodiments, the upper surface 178 of the slide 156 can be substantially free of freestanding liquid 169.

FIG. 7 is a side view of the pipettor 162 dispensing liquid 194 (e.g., reagent). After dispensing a desired volume of liquid 194, the actuator 192 can lower the opposable 154 onto the slide 156, and the opposable 154 can move liquid 199 across the slide 156.

Figure 8:
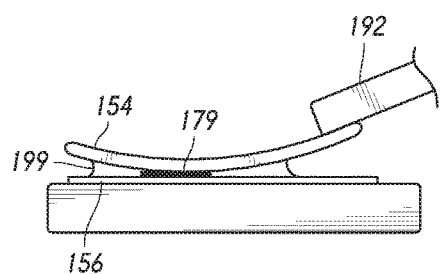
FIG. 8 is a view of liquid held between the opposable element and the slide.

FIG. 8 is a side view of the liquid 199 held between the opposable 154 and the slide 156 after the opposable 154 has been moved to the lowered position. The opposable 154 can be used to move the liquid 199 along the slide 156.

The method of FIGS. 4-8 can be used to apply a wide range of liquids. Liquids can be applied for pretreatment (e.g., protein-crosslinking, exposing nucleic acids, etc.), denaturation, hybridization, washing (e.g., stringency washing), detection (e.g., linking a visual or marker molecule to a probe), amplifying (e.g., amplifying proteins, genes, etc.), counterstaining, or the like. In various embodiments, the substances include, without limitation, stains (e.g., hematoxylin solutions, eosin solutions, or the like), wetting agents, probes, antibodies (e.g., monoclonal antibodies, polyclonal antibodies, etc.), antigen recovering fluids (e.g., aqueous- or non-aqueous-based antigen retrieval solutions, antigen recovering buffers, etc.), solvents (e.g., alcohol, limonene, or the like), or the like. Stains include, without limitation, dyes, hematoxylin stains, eosin stains, conjugates of antibodies or nucleic acids with detectable labels such as haptens, enzymes or fluorescent moieties, or other types of substances for imparting color and/or for enhancing contrast. Relatively small volumes of liquids can be dispensed using the pipettor 162 whereas relatively large volumes of liquids can be dispensed by the high-volume dispenser head 175. For example, the pipettors 160, 162 of FIG. 2 can dispense small volumes of liquid for individualized staining whereas the dispenser head 175 can dispense high volumes of bulk liquids. If the specimen 179 is a biological sample embedded in paraffin, the sample 178 can be deparaffinized using appropriate deparaffinizing fluid(s) dispensed by the dispenser head 175. After removing the deparaffinizing fluid(s), any number of substances can be sequentially applied to the specimen 179 using the dispenser head 175 and/or pipettor 162. In some embodiments, the pipettor 162 dispenses reagents, and the dispenser head 175 dispenses wash solutions to wash off the specimen and/or slide. Although the dispenser head 175 is described dispensing non-staining liquids, the dispenser head 175 can also dispense other types of liquids, including reagents. The pipettors 160, 162 are described dispensing reagents but can also dispense other liquids, such as wash solutions.

Figure 9:
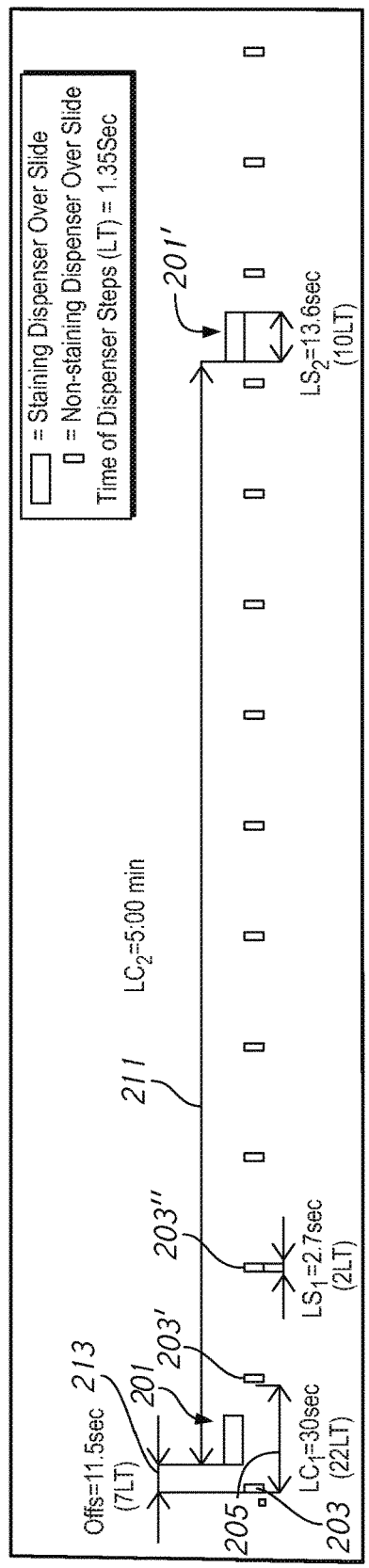
FIG. 9 shows a sequence for processing a specimen-bearing slide in accordance with an embodiment of the disclosed technology.

FIG. 9 shows lock steps relative to time for processing a slide in accordance with an embodiment of the disclosed technology. Generally, liquid dispensers can address the slide at different times. In a non-staining or high-frequency lock cycle 205, a dispenser addresses the slide for possible dispensing of liquid. The non-staining lock cycle 205 can include a lock step 203 in which a dispenser addresses the slide, as well as other lock steps (not shown) for addressing other slides. In a staining or low-frequency lock cycle 211, a dispenser can address the slide for possible dispensing of staining liquid. The non-staining and staining lock cycles 205, 211 can be repeated to periodically dispense liquids onto the slide, as detailed below.

At lock step 203 of the lock cycle 205, a dispenser can be positioned to dispense non-staining liquid onto the slide. (FIG. 4 shows one liquid dispenser in the form of the dispenser head 175 during such a lock step.) Liquid can be dispensed for the entire duration of the lock step 203. In other embodiments, liquid is dispensed for only a portion of the lock step 203. In yet other embodiments, liquid is not dispensed during the lock step 203. Once the lock step 203 is completed, the dispenser can be moved away from the slide. In the illustrated embodiment, the lock cycle 205 has a duration $LC_1$ equal to 30 seconds to index 20 slide positions and return to the same position, therefore the lock step 203 has a duration of approximately 2.7 seconds ($LS_1$=2.7 seconds is labeled for lock step 203"=30 seconds/ {20 stations movements+1 return movement} in this embodiment) such that the dispenser begins another lock cycle on the same slide after every 30 seconds (i.e., approximately 27.3 seconds after leaving the slide at lock step 203').

At lock step 201 of the lock cycle 211, a dispenser can be positioned to dispense staining liquid onto the slide. (FIGS. 6 and 7 show one liquid dispenser in the form of the pipettor 162 during such a lock step.) For the entire duration of the lock step 201 staining tasks may occur for one pipette (e.g., a pipette of pipettor 160 of FIG. 2) without collision with the other (i.e., pipettor 162 of FIG. 2). Such staining tasks can include, but are not limited to, aspirating fluid from a vial (e.g., vial 149a of FIG. 2), moving fluid to the specimen (e.g. specimen) or mixing station (e.g., mixing stations 165a, 165b of FIG. 2), and dispensing fluid in these locations. In other embodiments, liquid is dispensed for only a portion of the lock step 201. In yet other embodiments, liquid is not dispensed during the lock step 201. If liquid is not dispensed, the dispenser may not move and, in some embodiments, may be positioned at a standby position or other suitable location. In the illustrated embodiment, the lock step 201 has a duration of approximately 13.6 second ($LS_2$ of about 13.6 seconds labeled for lock cycle 201'), and the lock cycle 211 has a duration $LC_2$ of 5 minutes (e.g., 10× the timing of the non-staining lock step) in order to index all 20 slides of the illustrated embodiment. After completing the cycle 211 (i.e., after addressing a set of slides), the dispenser can return to the slide at lock step 201'. A lock cycle offset 213 can be selected to prevent any overlap between the lock step 201 and one or both lock steps 203, 203'. The periods of time of the lock steps of different lock cycles can be generally equal to one another to provide consistent processing. Other periods of time and offsets can be used, if needed or desired.

Figure 10:
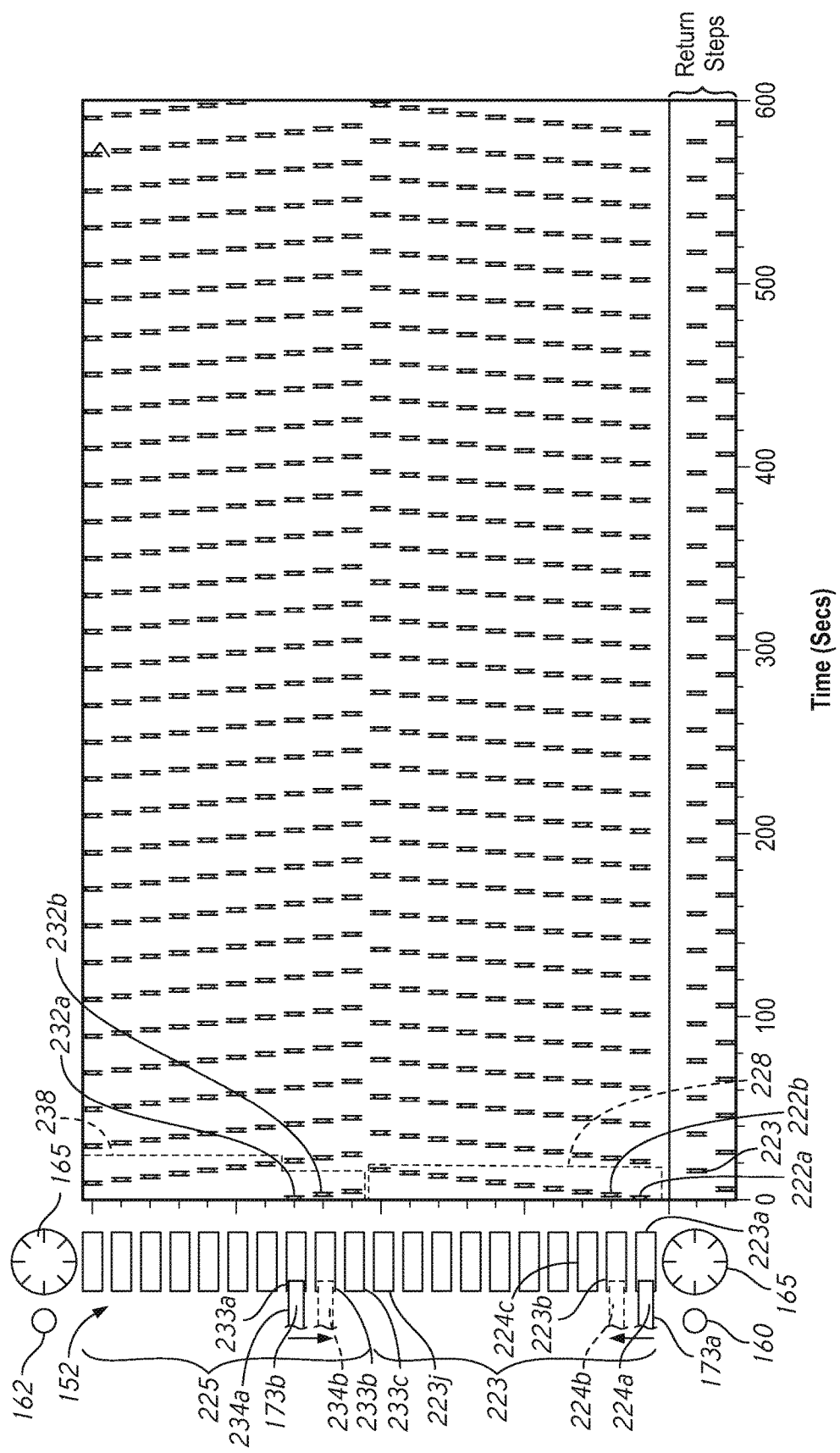
FIG. 10 is a top view of an array of slides and a plot of lock steps for dispensing liquids relative to time in accordance with an embodiment of the disclosed technology.

FIG. 10 is top view of a slide set 152 and a plot of lock steps relative to time in accordance with an embodiment of the disclosed technology. Two liquid dispenser apparatuses 173a, 173b (collectively "dispensers 173") can move (e.g., linearly) to sequentially dispense liquid onto the slides located at slide processing stations. A non-staining or secondary lock cycle 228 ("lock cycle 228") can include all the lock steps for addressing all the slides in the set 233. A lock step 222a corresponds to the dispenser 173a at a first position 224a for addressing the slide 223a. After addressing the slide 223a, the dispenser 173a moves to a second position 224b (illustrated in dashed line) for addressing a slide 223b, which corresponds to a lock step 222b. The dispenser 173a can be sequentially moved to address respective slides in the set 223 and can return to the initial dispense position 224a during a return lock step 223, which can have a duration equal to or different from the durations of other lock steps (e.g., lock step 222a).

Another non-staining or secondary lock cycle 238 can include all the lock steps for addressing all the slides in the set 225. At lock step 232a, the dispenser 173b can be positioned at a dispense position 234a for addressing a slide 233a. After addressing the slide 233a, the dispenser head 173b moves to a second position 234b (illustrated in dashed line) corresponding to a lock step 232b. The dispenser 173b can be moved to sequentially address the respective slides in the set 225 corresponding to the illustrated plotted lock steps. To avoid collisions, the dispensers 173a, 173b do not address adjacent slides (e.g., immediately adjacent slides or 2-3 neighbors away) at the same time. For example, movement of the dispenser 173a can be synchronized with movement of the dispenser 173b such that the dispensers 173a, 173b address the slides 223c, 223j, respectively, at different times. In FIG. 10, the dispenser 173b addresses the slide 233c while the dispenser 173a addresses the slide 223c. The number of slides (or slide processing stations) separating concurrently processed slides can be selected to avoid collisions between the components of mechanisms moving the dispensers 173a, 173b.

Figure 11:
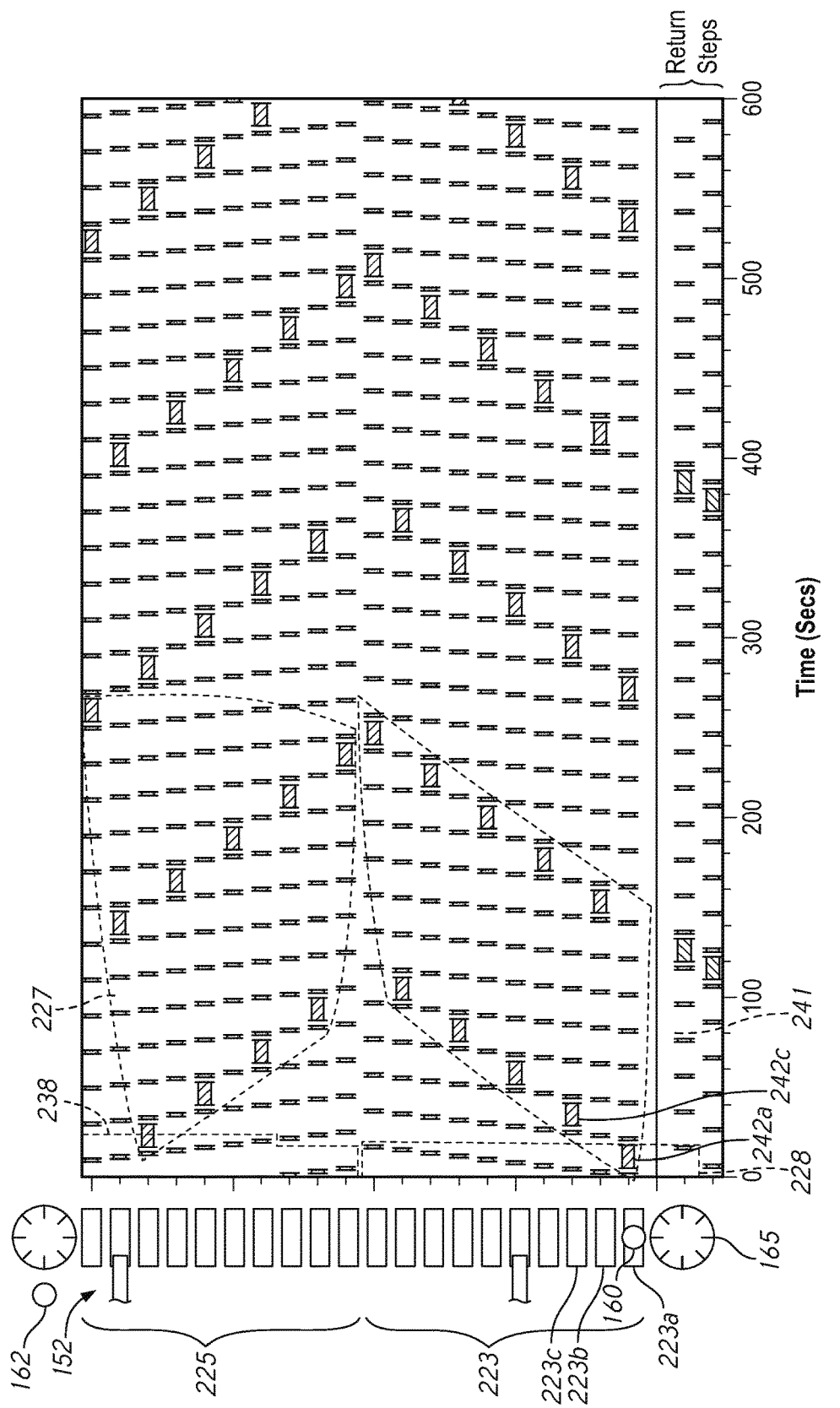
FIG. 11 is a top view of an array of slides and a plot of dual-locksteps relative to time in accordance with an embodiment of the disclosed technology.

FIG. 11 shows lock cycles for the dispensers 173a, 173b and lock cycles for the pipettors 160, 162 (shown schematically from above) relative to time in accordance with an embodiment of the disclosed technology. In a lock cycle 241, the pipettor 160 (illustrated above slide 223a) can sequentially address each slide in the set 223. The lock cycles 228, 238 of the dispensers 173a, 173b, respectively, can be synchronized with lock cycles 241, 227 of the pipettors 160, 162, respectively. At lock step 242a of the lock cycle 241, the pipettor 160 can address the slide 223a. After addressing the slide 223a, the pipettor 160 can obtain liquid (e.g., liquid from the mixing station 165) for delivery to the next slide 223c at lock step 242c. This process can be repeated to address each slide in the set 223. The lock cycle 241 can be repeated at a frequency that is different from the frequency of the lock cycle 228. For example, the lock cycle 228 can be performed at a first frequency that is at least twice the frequency of the lock cycle 241. As such, the lock cycle 228 can provide granularity for applying liquids at specific times to wash off specimens/slides, stop reactions, compensate for evaporative losses, or the like. In some embodiments, a ratio of the frequency of the lock cycle 228 to the frequency of the lock cycle 441 is equal to or greater than about the number of slides in the set 223. Thus, one or more lock cycles 228 can be performed for each lock step of the lock cycle 241.

Although the dispensers 160, 162 may be capable of colliding, they can be moved at different times to avoid such collisions. By way of example, as illustrated in FIG. 11 the lock cycles 241, 227 can be coordinated to dispense staining liquid alternatively onto slides in the set 223 using dispenser 160 and slides in the set 225 using dispenser 162 in order to avoid collisions between these dispensers. In some embodiments, there may be no overlap between the lock steps of the dispensers 160, 162. In other dispensing routines, there may be some overlap between the lock steps of the dispensers 160, 162.

FIG. 12 is a table of parameters for dual-lockstep processing with flow numbers (FN) −2, −1, 1, 2, 3, and 4 for first lock cycles/steps (i.e., the flow number may be adjusted in order to set the frequency relationship between the non-staining and staining lock cycles). It is envisioned that the first lock cycle time ("FLC" or "$LC_1$"), which governs the high frequency lock cycle, would be set as fast as possible, taking into account any physical limitations of the system. The FLC, however, can also be multiples of a minute, e.g., 15 sec., 20 sec., 30 sec. This will allow protocol steps to be easily rounded fractions of a minute, e.g., 3:20, 4:00, 15:30. If the FLC is an odd multiple of a minute, e.g., 23 sec., then it would be more difficult but still possible to calculate or set the FLC in multiples of 23 sec. This would mean if an incubation time was needed to be around 7-8 min., then the FLC would have to be set around 7:17 or 7:40, for example. For this reason it is envisioned that one would prefer to make the FLC a round number of seconds.

In the illustrated embodiment the FLC is 20 seconds or 30 seconds. This yields a first lock step time ("FLS" or "$LS_1$") that can be in a range of approximately 1.8 seconds to about 2.7 seconds for this embodiment based on the number of slides that each cycle must index ("n"), which is 10 for the illustrated embodiment (20 slides total, therefore 10 for each cycle in the 'dual' lock cycle algorithm). In some embodiments, the FLC can be in a range of about 10 seconds to the 30 seconds. The second lock steps time ("SLS" or "$LS_2$") can be in a range of about 10 seconds to about 14 seconds. For example, SLS can be equal to about 10.9 seconds, 11.8 seconds, 12.3 seconds, 12.7 seconds, or 13.6 seconds and second lock cycle ("SLC" or "$LC_2$") can be in a range of about 4 minutes to about 5 minutes. As previously mentioned other time periods can be selected.

Figure 13:
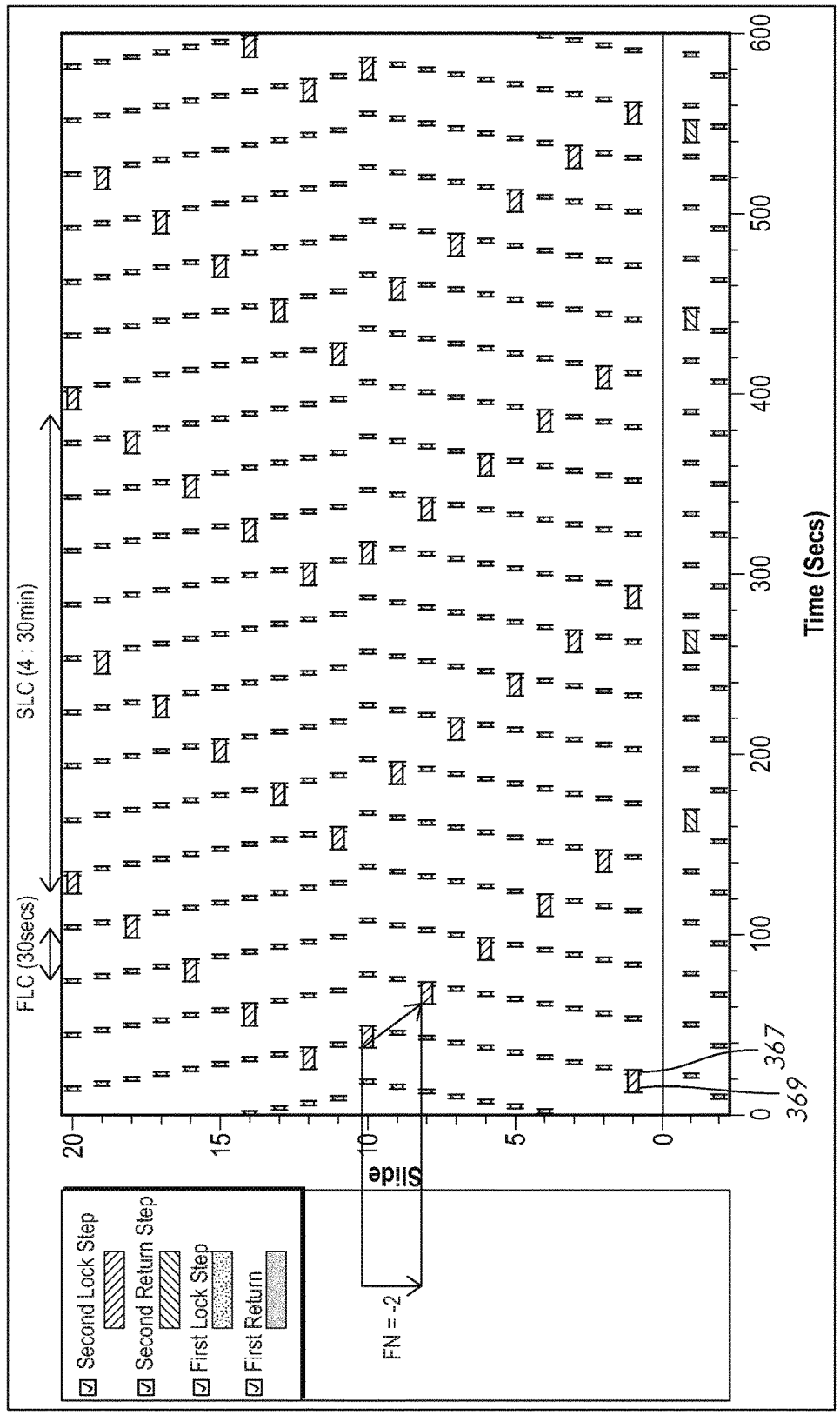
FIG. 13 is a plot of lock steps relative to time for a particular example of a flow number.
Figure 14:
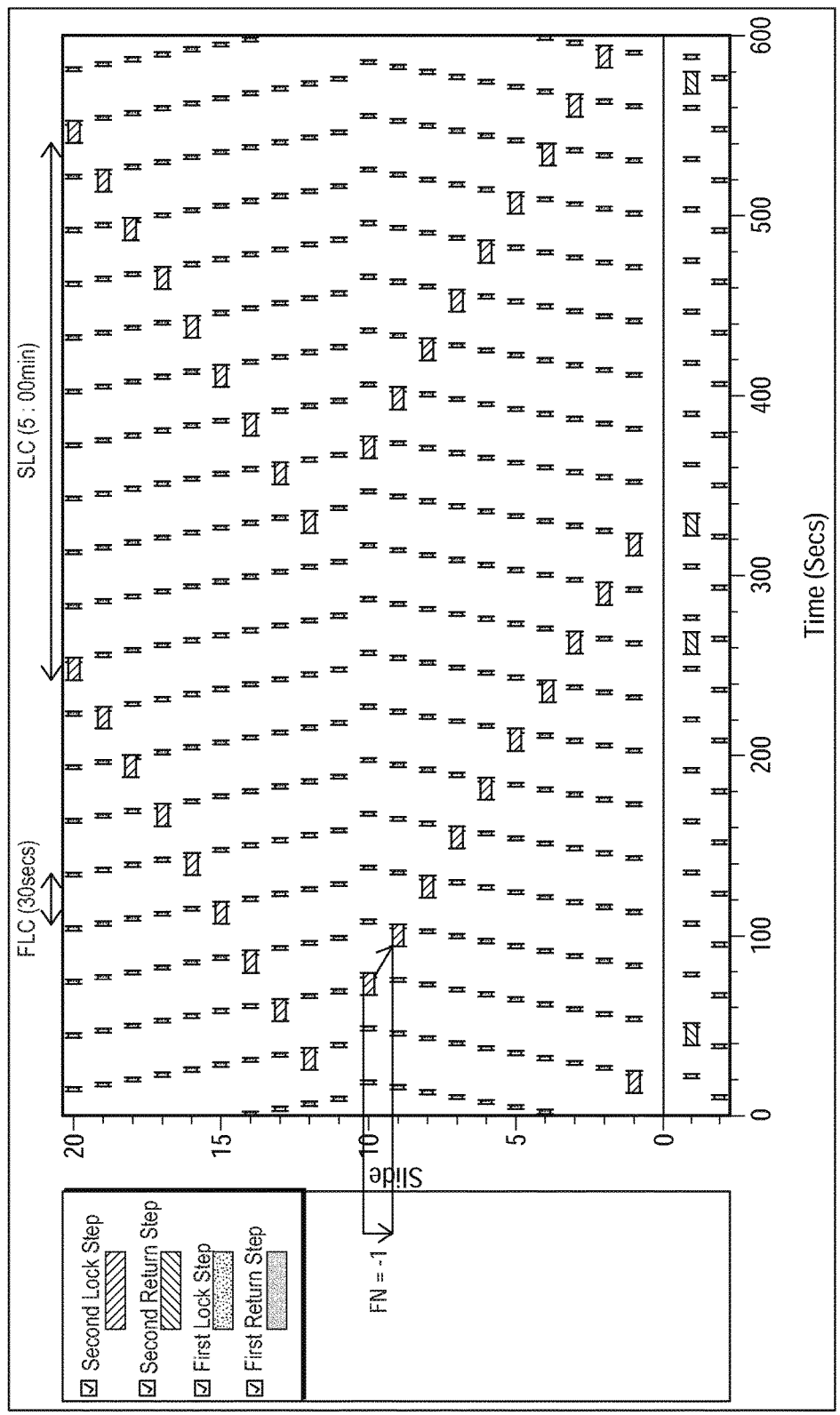
FIG. 14 is a plot of lock steps relative to time for a particular example of a flow number.
Figure 15:
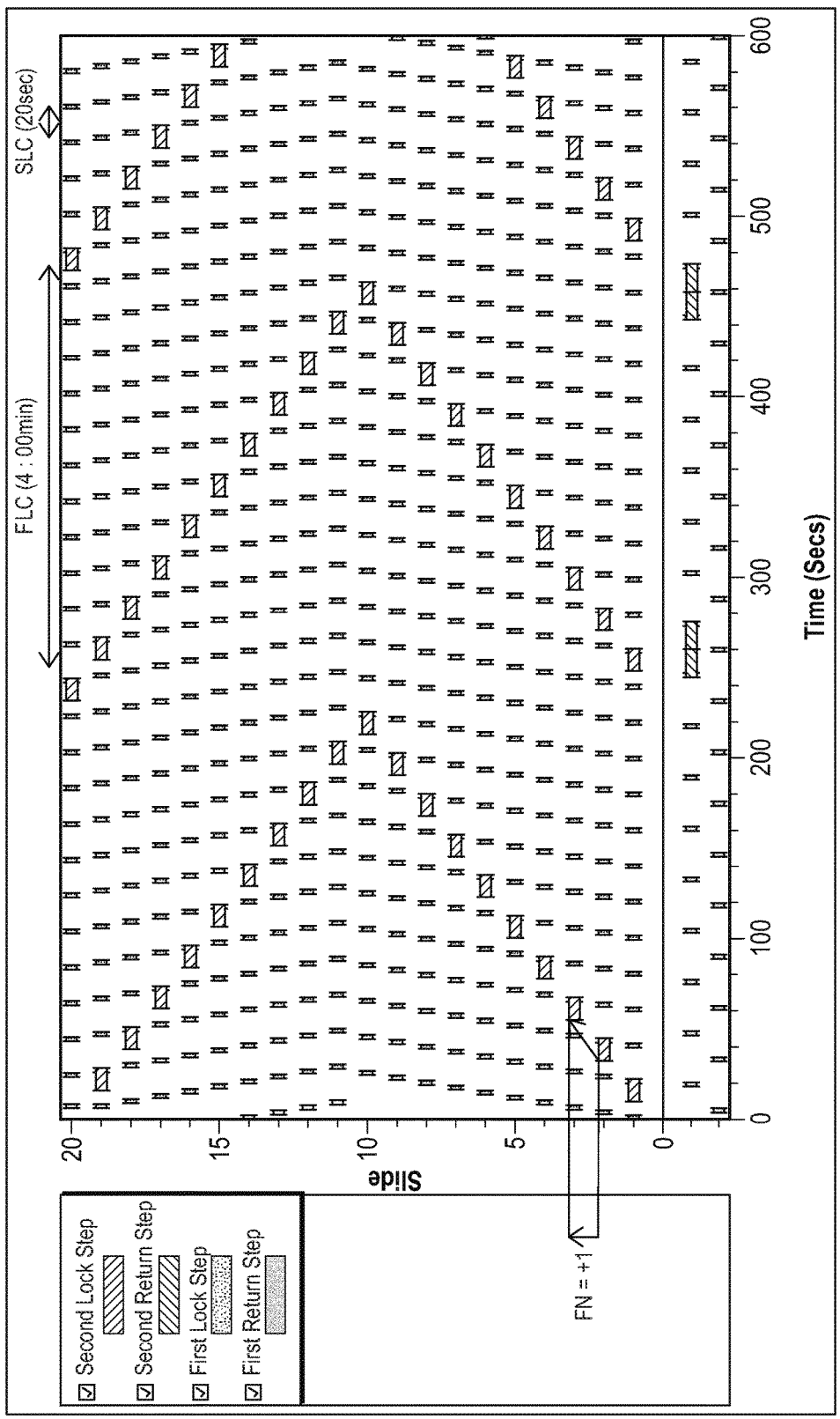
FIG. 15 is a plot of lock steps relative to time for a particular example of a flow number.
Figure 16:
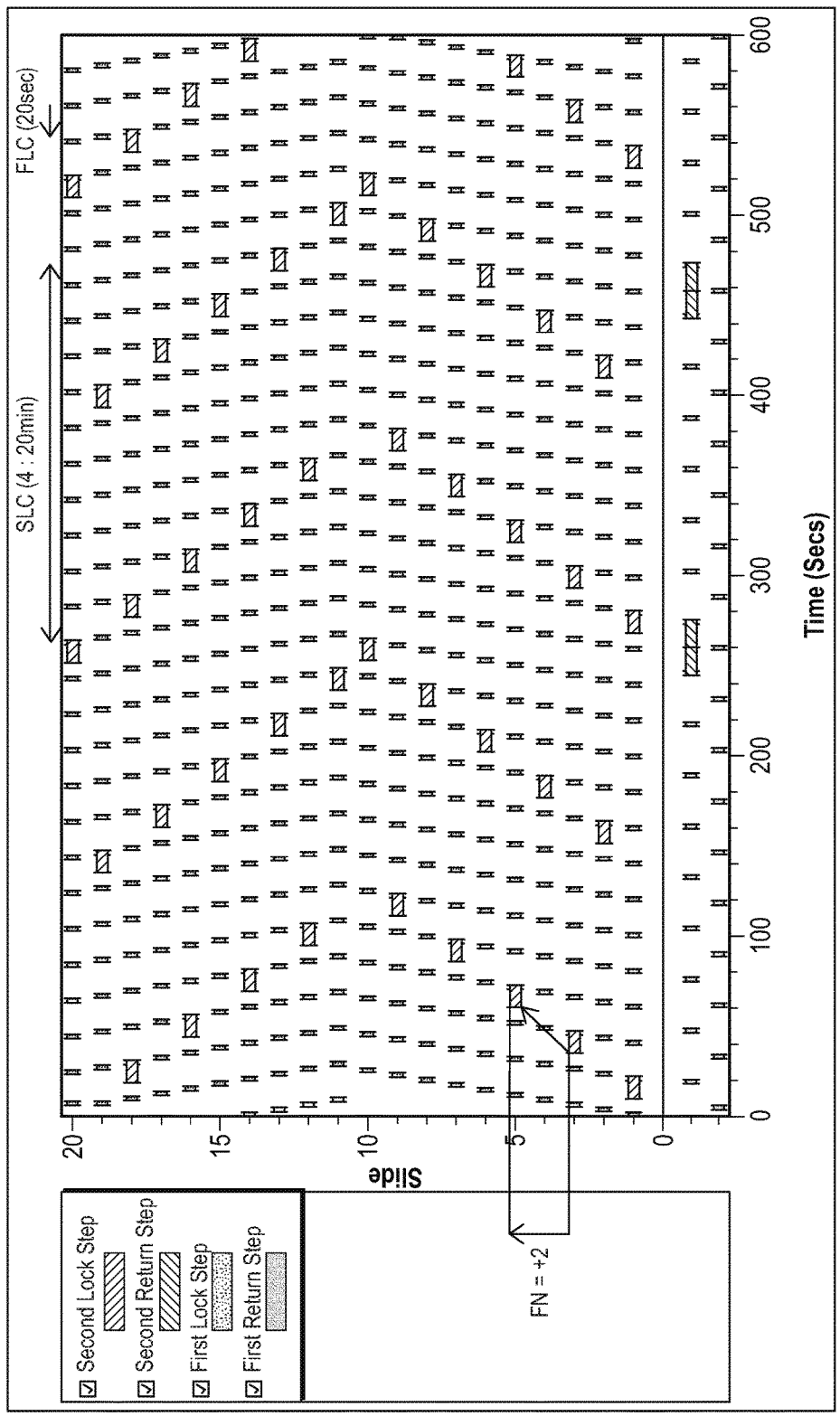
FIG. 16 is a plot of lock steps relative to time for a particular example of a flow number.
Figure 17:
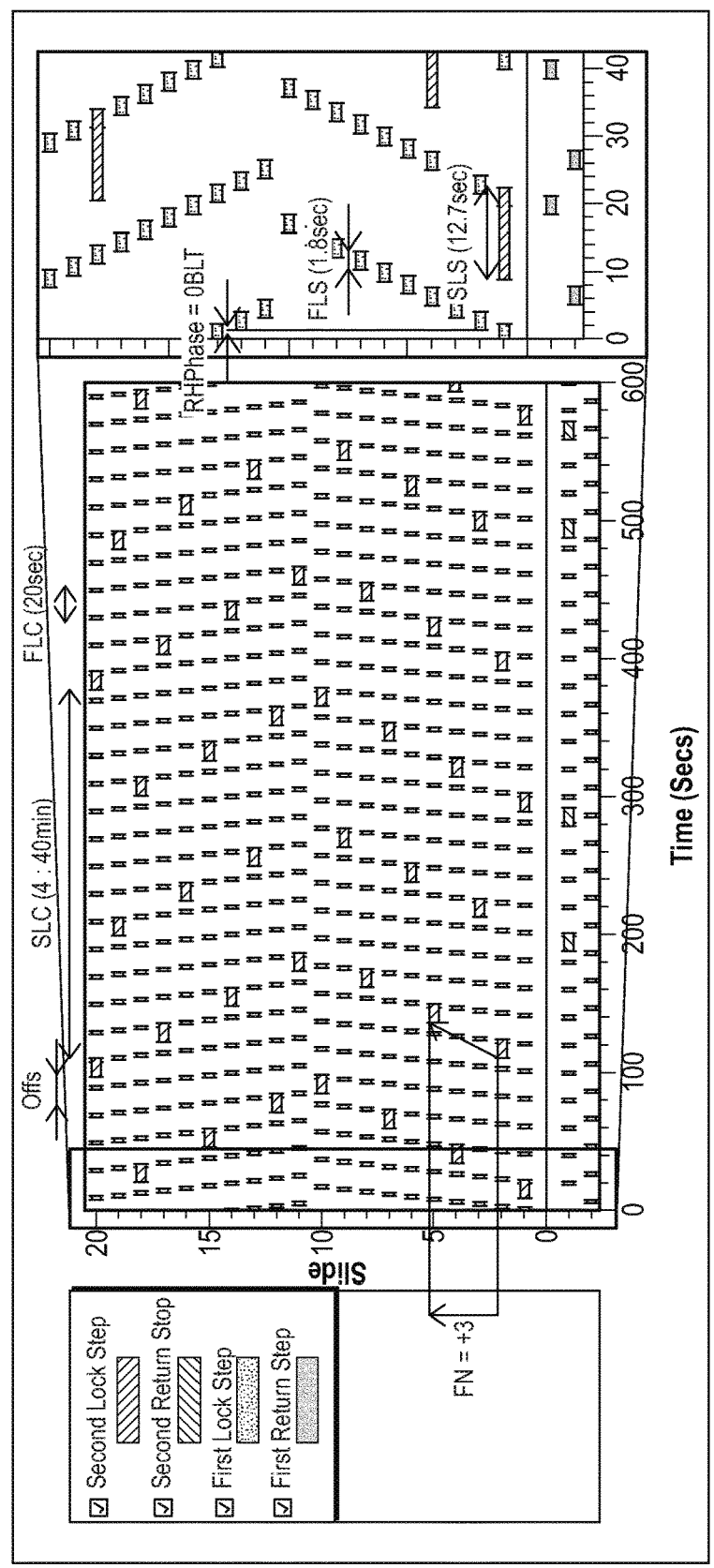
FIG. 17 is a plot of lock steps relative to time for a particular example of a flow number.
Figure 18:
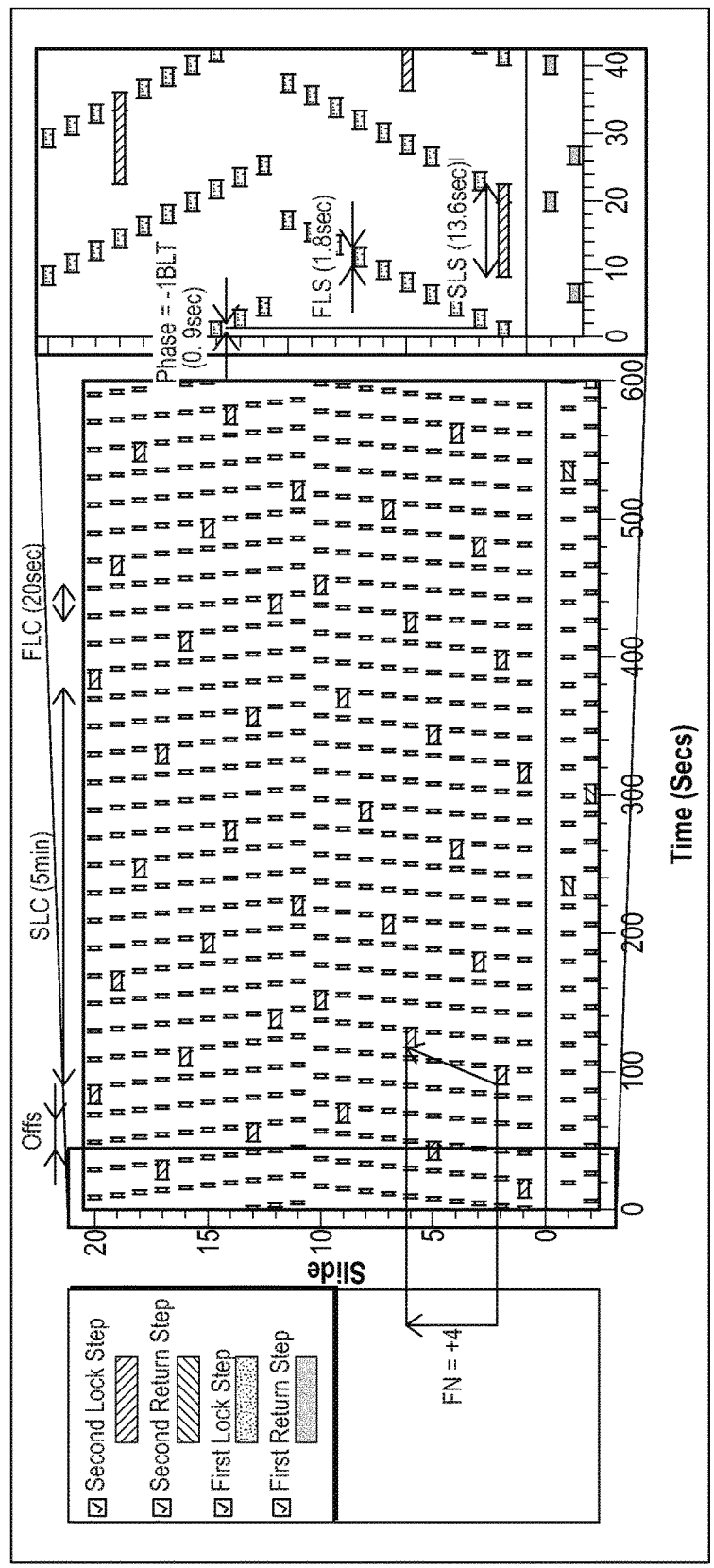
FIG. 18 is a plot of lock steps relative to time for a particular example of a flow number.

FIGS. 13, 14, 15, 16, 17, and 18 are lock cycle/step plots for flow numbers of −2, −1, 1, 2, 3, and 4, respectively, in accordance with an embodiment of the disclosed technology. The system 100 (FIG. 1) can process slides according to the lock cycles/steps shown in FIGS. 10-18. Although FIGS. 10-18 show exemplary time parameters, other time parameters can be used. FIGS. 17 and 18 show timing details of the lock steps. In some dispensing routines, there may be some overlap between the lock steps. FIG. 13 shows overlapping lock steps 367, 369. Different batches of slides can be processed using different dual-lockstep process to optimize performance. For example, one batch of slides can be processed using the multistep processing shown in FIG. 13 and another batch of slides can be processed using the multistep processing shown in FIG. 14. The controller 144 of FIG. 1 can contain instructions for performing the various lock step sequences of FIGS. 13, 14, 15, 16, 17, and 18. Additionally, while FIGS. 10-11, 13-18 show embodiments whereby the left and right dispensers index slide processing positions in counter-directions, i.e., both move towards the center position before returning to the outer positions, it is also possible that they may be indexed to move in the same direction.

Figure 19:
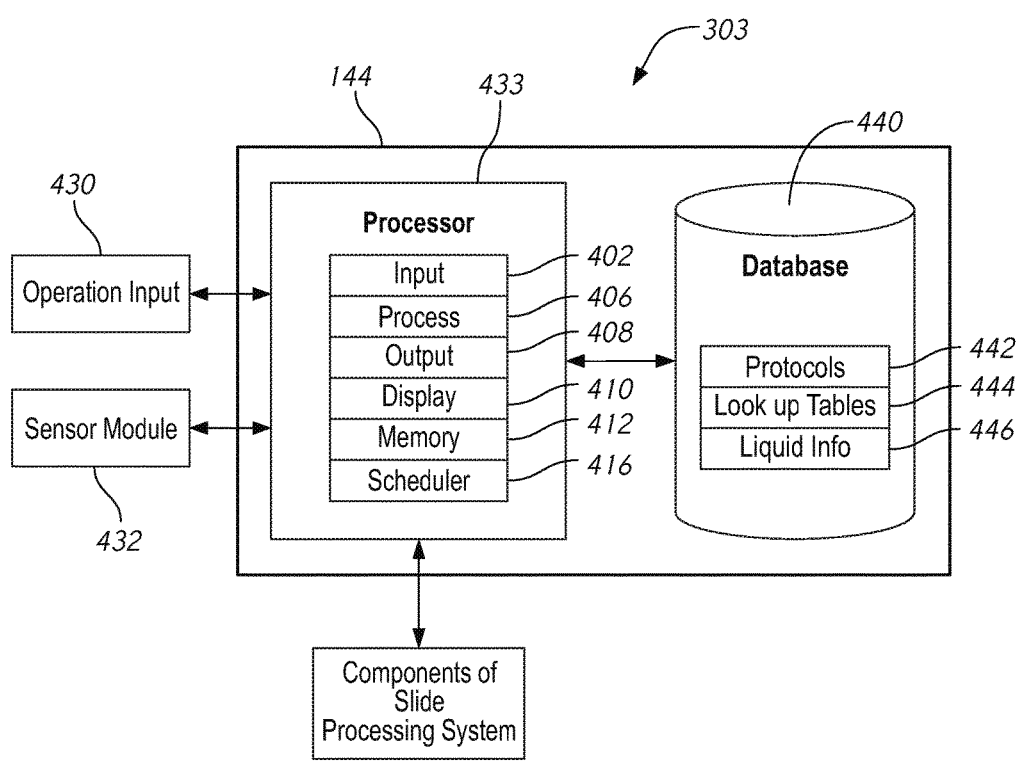
FIG. 19 is a block diagram showing a computing system in accordance with an embodiment of the disclosed technology.

FIG. 19 is a block diagram showing a computing system 303 in accordance with an embodiment of the present disclosure. The computing system 303 can include the controller 144 with components in the form of computer programs, procedures, or processes written as source code in a programming language and may be presented for execution by a processor (e.g., CPU). The various implementations of the source code and object byte codes may be stored on a computer-readable storage medium. In some embodiments, the controller 144 has a programmable processor 433 and a database 440. The processor 433 may include an input module 402, a process module 406, an output module 408, a display module 410 (e.g., a screen, a monitor, etc.), memory 412, and scheduler module 416 interconnected with one another. The input module 402 can receive operation input 430, such as desired staining characteristics, processing times, or other information, and communicates the information to other components. The input module 402 can also receive sensor readings 432 from sensors (e.g., temperature sensors, slide presence sensors, bar code sensors, etc.) or other detectors.

The process module 406 can receive information (e.g., available reagents, slide locations, temperature set points, power settings, environmental information such as ambient temperatures and/or humidity, processing protocols, etc.) from memory 412 and/or database 440. The process module 406 can determine lock step parameters, lock step start times, lock step end times, deliver path coordination, etc. Memory 412 can also store program instructions. One stored sequence of program instructions can be used to contact the specimen with a wash and another sequence of program instructions can be used to apply a reagent (e.g., a stain) to the specimen. The programmable processor 433 can execute such program instructions to perform synchronized lock cycles (e.g., lock cycles discussed in connection with FIGS. 11, 13, 14, 15, 16, 17, and 18).

The scheduler module 416 can include one or more computation routines or algorithms for generating schedules based on predetermined values, such as lock increments. Lock increments can be the resolution of timing or actions of components. In some embodiments, the lock increments can be the smallest resolution of one of the dispensers. A first lock step time (FLS) allocated to a first dispenser (e.g., a non-staining/secondary dispenser) to dispense liquid to a single slide can be determined as illustrated in FIG. 12 according to the following formula:

$$FLS = FLC/(n+FR) \qquad \text{(Formula 1)}$$

where FLC is a first lock cycle time of the first lock cycle, FR is a constant number (often 1 as illustrated in this embodiment) of lock steps allocated to 'return time' (e.g., the number of lock steps needed to physically move a dispenser across its range of motion to 'return' it to a starting position), and n is a total number of slides to be processed by the first dispenser. The total number of slides n for the embodiment of FIGS. 9 and 10 is 10, but the total number n can be greater or less than 10 (e.g., 6 for 12 slide processing stations).

A second lock step time (SLS) allocated to a second dispenser (e.g., a staining/primary dispenser) to dispense liquid onto respective slides for a second lock cycle can be determined as illustrated in FIG. 12 according to the following formula:

$$SLS=(n+FR+FN)\times FLS/2 \quad \text{(Formula 2)}$$

where n is the total number of slides to be processed by the first dispenser, FR is a constant number of lock steps allocated to 'return time', FN is a flow number, and FLS is the step time of the first dispenser (computed in Formula 1).

The scheduler module 416 can determine schedules based on flow numbers (e.g., flow numbers equal to −2, −1, 1, 2, 3, and 4 as shown in FIGS. 13, 14, 15, 16, 17, and 18, respectively) although other flow numbers can also be used. As outlined in Formula 2, the flow number (FN) will govern the timing (or frequency) of the Second Lock Step (SLS) with respect to the First Lock Step (FLS). In addition advantageously, flow (i.e., movement) of the second lock step dispensers is also influenced by Flow Number and can be selected to prevent collisions between dispenser apparatuses (e.g., the dispenser apparatuses 172, 173 of FIG. 2 capable of colliding without proper scheduling). One dispenser can sequentially address adjacent slides one-by-one while another dispenser can address slides based on a flow number. In some embodiments, the secondary or bulk lock steps can be fixed, and the primary or staining lock steps can be adjusted by choosing a flow number that corresponds to a specific configuration offsetting the timing and/or order of slide address by the primary dispenser. In some embodiments, the secondary or bulk lock steps can be adjusted, and the primary or staining lock steps can be fixed. This ability to select the order and timing of slide address allows the system to handle independent slide processing more quickly and efficiently without sacrificing uniform distribution of resources.

The database 440 can organize information, including protocols 442, lookup tables 444, liquid information 446, and so forth. The protocols 442 can include, without limitation, specimen conditioning protocols, antigen retrieval protocols, hematoxylin and eosin stain (H&E) staining protocols, other types of protocols for preparing specimens for visual inspection, fluorescent visualization, microscopy, microanalyses, mass spectrometric methods, imaging (e.g., digital imaging), or other analytical or imaging methods. Lookup tables 444 can include, without limitation, reagent recipes, processing temperatures (e.g., target tissue processing temperatures), timing information (e.g., lock cycle periods, lock step periods, etc.), and other parameters. The liquid information 446 can be information about the characteristics of wash solutions, reagents, etc. In some embodiments, the database information is inputted by the user. In other embodiments, database information is obtained from containers, such as reagent containers. Any type of database organization may be utilized, including a flat file system, hierarchical database, relational database, or distributed database.

With continued reference to FIG. 19, the controller 144 can command components of the specimen processing system 100 to wash slides/specimens, apply reagents, and apply supplemental liquids. During staining, volumes of stain can be kept in equilibrium ranges. If the volume of liquid on a slide is above the equilibrium volume range, the liquid can evaporate at a relatively high rate and may significantly change the concentration of the liquid. If the volume of liquid is below the equilibrium volume range, there may be an insufficient volume of liquid to adequately process the specimen. An insufficient volume of liquid can also result in an undesirably low amount of liquid agitation during processing. The equilibrium volume range can be selected based on the composition of the liquid, desired processing temperature, or desired agitation of the liquid. An equilibrium volume of the liquid can correspond to a fluid volume (at a certain temperature or range of temperatures) that provides full coverage of the specimen while keeping evaporative losses below a target level. A dispenser (e.g., dispenser head 175 of FIG. 3) can function as a replenishment device that periodically supplements the liquid at a fixed or variable rate (e.g., a rate based on the evaporation rate) to keep the volume of the liquid within the equilibrium volume range. By way of example, the dispenser head 175 of FIG. 4 can replenish liquid to keep the volume of liquid 199 (FIG. 8) within the equilibrium volume range. With a target processing temperature, or temperature range, and a total evaporation rate, the controller 144 of FIG. 19 can determine a target range of equilibrium volumes and lock cycle/step schedules.

Processing protocols may require different opposable rolling speeds and different liquid volumes in order to meet various processing criteria (e.g., chemical requirements, uptake requirements, solubility limitations, viscosity, or the like). If the specimen is a paraffin embedded specimen, a relatively small volume of de-waxing solution (e.g., 12 microliters of xylene) can be delivered onto the slide during a non-staining/secondary lock step. After dewaxing, a relatively large volume of reagent can be delivered onto the slide during another staining lock step. For example, a dispenser (e.g., pipettor 162 of FIG. 7) can deliver a volume of about 125 microliters to about 180 microliters of stain onto the slide and is subsequently removed using a wash solution from a dispenser (e.g., dispenser 175 of FIG. 4).

Lock step processing can be used to perform assay steps (e.g., antibody and chromogen assays) at relatively low temperatures. Slide holder platens disclosed herein can control the specimen and/or processing liquid at a temperature in a range of about 35° C. to about 95° C. In one embodiment, the liquid and/or specimen is kept at a temperature of about 37° C. The dispenser (e.g., dispenser apparatus 173 of FIG. 2) can deliver supplemental liquid to maintain a target volume of about 30 microliters to about 350 microliters. In some protocols, the dispenser delivers supplemental liquid at a rate of about 4 to about 5.1 microliters per minute to about 5.6 microliters per minute. In such embodiments, the volume of the liquid on the slide can be kept in a range of about 90 microliters to about 175 microliters over about a 15 minute period based on a relative humidity of about 10%-90%, an ambient temperature of about 15° C. to about 32° C., with an average slide temperature tolerance of about ±1° C., and an opposable rolling speed of about 25 to 60 millimeters per second. The evaporation rate may be generally proportional to the rolling speed. If the rolling speed is about 20 millimeters per second, a replenish rate of about 3.8 microliters per minute to about 4.2 microliters per minute can maintain a volume of about 115 microliters to about 200 microliters. If the rolling speed is about 40 millimeters per second, a replenish rate of about 5.1 microliters per minute to about 5.6 microliters per minute can maintain a volume of the liquid of about 115 microliters to about 200 microliters. At a high rolling speed of about 90 millimeters per second, the replenish rate can be about 7.6 microliters per minute to about 8.4 microliters per minute to maintain a volume of about 110 microliters to about 200 microliters. For targeted retrieval, the rolling speed of the opposable can be about 100 millimeters per second and the replenish rate can be 72 microliters per minute. For antigen retrieval, the rolling speed can be about 180 millimeters per second and the replenish rate can be about 105 microliters per minute. Other replenish rates can be selected based on the processing conditions.

From the foregoing, it will be appreciated that specific embodiments of the invention have been described herein for purposes of illustration, but well-known structures and functions have not been shown or described in detail to avoid unnecessarily obscuring the description of at least some embodiments of the invention. The systems, apparatuses, and components described herein can perform a wide range of processes for preparing biological specimens for analysis. The scheduling and methods disclosed herein can be used with different types of specimen processing systems with apparatuses configured to deliver liquid onto stationary slides, slides that are moved periodically or continuously throughout processing, or the like. Where the context permits, singular or plural terms may also include the plural or singular term, respectively. Unless the word "or" is associated with an express clause indicating that the word should be limited to mean only a single item exclusive from the other items in reference to a list of two or more items, then the use of "or" in such a list shall be interpreted as including (a) any single item in the list, (b) all of the items in the list, or (c) any combination of the items in the list. The singular forms "a," "an," and "the" include plural referents unless the context clearly indicates otherwise. Thus, for example, reference to "a specimen" refers to one or more specimens, such as two or more specimens, three or more specimens, or four or more specimens.

The various embodiments described above can be combined to provide further embodiments. The embodiments, features, systems, devices, materials, methods, and techniques described herein may, in some embodiments, be similar to any one or more of the embodiments, features, systems, devices, materials, methods, and techniques described in International App. Nos. PCT/US2010/056752; PCT/EP2013/077557; PCT/US2013/077162; PCT/EP2013/077559; PCT/EP2013/077560, PCT/US2013/077177; PCT/EP2013/077649; and PCT/US2013/077192, all of which are incorporated by reference in their entireties. For example, the slide processing stations disclosed herein can be the slide processing stations or specimen processing stations disclosed in International App. No. PCT/US2013/077162 filed Dec. 20, 2013. In addition, the embodiments, features, systems, devices, materials, methods, and techniques described herein may, in certain embodiments, be applied to or used in connection with any one or more of the embodiments, features, systems, devices, materials, methods, and techniques disclosed in the above-mentioned patents and applications. Aspects of the disclosed embodiments can be modified, if necessary, to employ concepts of the various above-mentioned patents, applications, and publications to provide yet further embodiments. All applications listed above are incorporated herein by reference in their entireties.

These and other changes can be made to the embodiments in light of the above-detailed description. Any claims intended to be treated under 35 U.S.C. § 112, ¶ 6 will begin with the words "means for", but use of the terms "step" or "for" in any other context is not intended to invoke treatment under 35 U.S.C. § 112, ¶6. For example, the term "lock step" does not invoke treatment under 35 U.S.C. § 112, ¶6. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An automated method for processing specimen-bearing microscope slides, the automated method comprising:
delivering a plurality of specimen-bearing microscope slides to respective slide processing stations;
repeatedly performing a first lock cycle that includes positioning a first dispenser sequentially at a plurality of first dispense positions for delivering liquid onto respective slides; and
performing a second lock cycle that includes positioning a second dispenser sequentially at a plurality of second dispense positions for delivering liquid onto respective slides,
wherein the second lock cycle is synchronized with the first lock cycle to prevent any collision between the first dispenser and the second dispenser while simultaneously performing the first lock cycle and the second lock cycle,
the automated method further comprising:
determining a first lock step time (FLS) for each of a plurality of first lock steps of the first lock cycle as follows:

$$FLS=FLC/(n+FR)$$

where FLC is a first lock cycle time of the first lock cycle, FR is a constant number of lock steps allocated to physically return the first dispenser through its range of motion, and n is a total number of the slides to be processed by the first dispenser;
determining a second lock step time (SLS) for each of a plurality of second lock steps of the first lock cycle (FLS) as follows:

$$SLS=(n+FR+FN)\times FLS/2$$

where n is the total number of the slides to be processed by the first dispenser, FR is the constant number of lock steps allocated to physically return the first dispenser through its range of motion, FN is a flow number, and FLS is the first lock step time;
determining a second lock cycle time (SLC) for each of a plurality of second lock steps of the second lock step (SLS) as follows:

$$SLC=SLS\times(n+FR)\times 2$$

where n is the total number of slides to be processed by the first dispenser, FR is the constant number of lock steps allocated to physically return the first dispenser through its range of motion, and SLS is the second lock step time; and
synchronizing the first lock steps with the second lock steps based on the flow number (FN) to deliver liquid from the first dispenser and liquid from the second dispenser at different times.

2. The automated method of claim 1, further comprising synchronizing the second lock cycle with the first lock cycle to prevent any collision between a first dispenser apparatus and a second dispenser apparatus that are capable of colliding when the first dispenser apparatus moves the first dispenser and/or when the second dispenser apparatus moves the second dispenser.

3. The automated method of claim 1, wherein:
performing the first lock cycle includes delivering non-staining liquid from the first dispenser onto each of the slides, and
performing the second lock cycle includes delivering liquid from a robotic pipettor of the second dispenser onto each of the slides.

4. The automated method of claim 1, further comprising synchronizing a plurality of first lock steps of the first lock cycle with a plurality of second lock steps of the second lock cycle to prevent simultaneous delivery of liquid from the first and second dispensers onto the same slide.

5. The automated method of claim 1, wherein:
the first lock cycle includes a plurality of first lock steps, wherein each of the plurality of first lock steps corresponds to positioning the first dispensing at a respective one of the first dispense positions and has a first period of time,
the second lock cycle includes a plurality of second lock steps, wherein each of the plurality of second lock steps corresponds to positioning the second dispensing at a respective one of the second dispense positions and has a second period that is different from the first period of time.

6. The automated method of claim 1, further comprising performing the first lock cycle at a frequency that is at least twice a second frequency at which the second lock cycle is performed.

7. The automated method of claim 1, further comprising synchronizing the first and second lock cycles such that the first and second dispensers are located at the first and second dispense positions for each slide at different times.

8. The automated method of claim 1, further comprising performing the first lock cycle each time the second dispenser is moved to one of the second dispense positions.

9. The automated method of claim 1, further comprising:
repeatedly performing additional first lock cycles using additional first dispensers; and
repeatedly performing additional second lock cycles using additional second dispensers such that movement of the additional second dispensers is coordinated with movement of the additional first dispensers.

10. The automated method of claim 1, wherein FN is an integer.

11. The automated method of claim 1, wherein FLC is any whole number of seconds selected to support one or more tasks associated with non-staining operations and constrained by physical limitations of the one or more tasks.

12. The automated method of claim 1, wherein FLC is about 30 seconds.

13. The automated method of claim 1, wherein SLC is a whole number of seconds and an integer multiple of FLC governed by selection of FN.

14. An automated slide processing apparatus, comprising:
a plurality of slide processing stations configured to hold respective specimen-bearing microscope slides;
a first dispenser apparatus movable relative to the slide processing stations and configured to sequentially dispense liquid onto the slides located at the slide processing stations;
a second dispenser apparatus movable relative to the slide processing stations and configured to sequentially dispense liquid onto each of the slides such that the first dispenser apparatus and the second dispenser apparatus deliver liquid onto each of the slides at different times; and
a controller in communication with the first dispenser apparatus and the second dispenser apparatus, the controller including a computer-readable medium containing instructions for performing a process comprising:
performing a first lock cycle that includes positioning the first dispenser apparatus sequentially at a plurality of first dispense positions for delivering liquid onto each of the slides located at the slide processing stations; and
performing a second lock cycle that includes positioning the second dispenser apparatus sequentially at a plurality of second dispense positions for delivering liquid onto each of the slides, wherein the second lock cycle is synchronized with the first lock cycle to prevent any collision between the first dispenser apparatus and the second dispenser apparatus while simultaneously performing the first and second lock cycles,
wherein the first dispenser apparatus includes:
a first non-staining dispenser movable along a first set of the slide processing stations to dispense liquid sequentially onto the slides at the first set of the slide processing stations, and
a second non-staining dispenser movable along a second set of the slide processing stations to dispense liquid sequentially onto the slides at the second set of the slide processing stations, and
wherein the second dispenser apparatus includes:
a first staining dispenser movable along a first set of the slide processing stations to dispense liquid sequentially onto the slides at the first set of the slide processing stations, and
a second staining dispenser movable along a second set of the slide processing stations to dispense liquid sequentially onto the slides at the second set of the slide processing stations, and
the controller includes a computer-readable medium containing instructions for performing the automated method of claim 1.

15. The automated slide processing apparatus of claim 14, wherein the controller in communication with the first dispenser apparatus and the second dispenser apparatus is configured and contains instructions for synchronizing a plurality of first lock steps for the first dispenser apparatus with a plurality of lock steps for the second dispenser apparatus to prevent simultaneous delivery of liquid from the first dispenser apparatus and the second dispenser apparatus onto the same slide.

* * * * *